United States Patent
Choi et al.

(10) Patent No.: US 9,688,740 B2
(45) Date of Patent: Jun. 27, 2017

(54) MUTANT CTLA4 GENE TRANSFECTED T CELL AND COMPOSITION INCLUDING SAME FOR ANTICANCER IMMUNOTHERAPY

(71) Applicant: NATIONAL CANCER CENTER, Gyeonggi-do (KR)

(72) Inventors: Kyungho Choi, Gyeonggi-do (KR); Jaehun Shin, Seoul (KR); Sang-Jin Lee, Seoul (KR)

(73) Assignee: National Cancer Center, Gyeonggi-Do (KR)

( * ) Notice: Subject to any disclaimer, the term of this patent is extended or adjusted under 35 U.S.C. 154(b) by 0 days.

(21) Appl. No.: 14/354,562

(22) PCT Filed: Oct. 26, 2012

(86) PCT No.: PCT/KR2012/008878
§ 371 (c)(1),
(2) Date: Apr. 26, 2014

(87) PCT Pub. No.: WO2013/062365
PCT Pub. Date: May 2, 2013

(65) Prior Publication Data
US 2014/0242049 A1    Aug. 28, 2014

(30) Foreign Application Priority Data

Oct. 26, 2011 (KR) .................. 10-2011-0109729
Oct. 26, 2012 (KR) .................. 10-2012-0119603

(51) Int. Cl.
*A01N 63/00* (2006.01)
*C07K 14/705* (2006.01)

(52) U.S. Cl.
CPC .... *C07K 14/70521* (2013.01); *C07K 2319/00* (2013.01)

(58) Field of Classification Search
CPC .............................................. C07K 14/70521
USPC ..................................................... 424/93.21
See application file for complete search history.

(56) References Cited

U.S. PATENT DOCUMENTS

| 6,090,914 A | 7/2000 | Linsley et al. |
| 7,700,556 B2 | 4/2010 | Peach et al. |
| 7,744,875 B2 | 6/2010 | Lowy et al. |
| 8,026,224 B2 | 9/2011 | Ostrand-Rosenberg et al. |

FOREIGN PATENT DOCUMENTS

| JP | H04-502009 A | 4/1992 |
| WO | 9005541 A1 | 5/1990 |
| WO | WO 03/008583 A2 * | 1/2003 | ............ C12N 15/12 |
| WO | WO 2005/014612 A1 * | 2/2005 | ............ C07H 21/04 |
| WO | 2010097597 A1 | 9/2010 | |
| WO | 2013/019615 A2 | 2/2013 | |

OTHER PUBLICATIONS

Linsley et al., 1992, J. Exp. Med. Vo. 176, pp. 1595-1604.*
van Wilk et al., 2007, J. Immunology, vol. 178, pp. 6894-6900.*
Hueber et al. (2006, Immunology and Cell Biology, vol. 84, pp. 51-58).*
Loskog et al. (2006, Leukemia, vol. 20, pp. 1819-1828).*
International Search Report.
Masteller E. L. et al, "Structural analysis of CTLA-4 function in vivo", J Immunol. May 15, 2000;164(10):5319-27.
Yin L. et al., "Short cytoplasmic SDYMNM segment of CD28 is sufficient to convert CTLA-4 to a positive signaling receptor", J Leukoc Biol. Jan. 2003; 73(1):178-82.
Cartellieri, M. et al., "Chimeric antigen receptor-engineered T cells for immunotherapy of cancer," Journal of Biomedicine and Biotechnology, vol. 2010, Article ID 956304, 13 pages (2010) doi: 10.1155/20 10/956304. See abstract, figures 1-3.
Shin, J .H. et al., "Positive conversion of negative signaling of CTLA4 potentiates antitumor efficacy of adoptive T-cell therapy in murine tumor models," Blood, vol. 119(24), pp. 5678-87 (Online Apr. 26, 2012) See the entire document.
Office action issued on Jun. 16, 2015 from Japan Patent Office in a counterpart Japan Patent Application No. JP2014-538714.
Xuewu Zhang et al., Structural and Functional Analysis of the Costimulatory Receptor Programmed Death-1, Immunity. vol. 20, pp. 337-347, Mar. 2004.
Kevin M. Dennehy et al, Cutting Edge: Monovalency of CD28 Maintains the Antigen Dependence of T Cell Costimulatory Responses, The Journal of Immunology, 2006 176:5725-5729; doi:10.4049/jimmunol.176.10.5725.
Office action issued on Mar. 1, 2016 from Japan Intellectual Property Office in a counterpart Japan Patent Application No. 2014-538714.
D J Lenschow et al., CD28/B7 System of T Cell Costimulation, Annu. Rev. Immunol., 1996, vol. 14, p. 233 to p. 258.
Leach DR et al., Enhancement of antitumor immunity by CTLA-4 blockade. Science, New Series, vol. 271, No. 5256 (Ma . 22, 1996), pp. 1734-1736.

* cited by examiner

Primary Examiner — Thaian N Ton
Assistant Examiner — David A Montanari
(74) Attorney, Agent, or Firm — Lathrop & Gage LLP

(57) ABSTRACT

A transformed T-cell for T-cell therapy, and a composition including the same for anticancer immunotherapy. More particularly, the transformed T-cell is characterized by the transfection of a gene for coding a chimera protein. The T-cell, to which the gene for coding the chimera protein is transected, may improve the therapeutic effects induced by immune tolerance of cancer cells, and furthermore maximize anti-cancer effects by activating signal transduction to induce the activation of T-cells. Also, the disclosure allows treatments that minimize side effects such as the development of autoimmune diseases due to systematic T-cell activation.

13 Claims, 15 Drawing Sheets

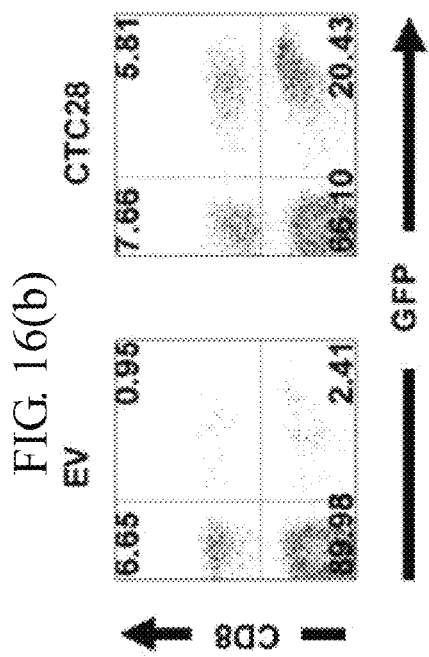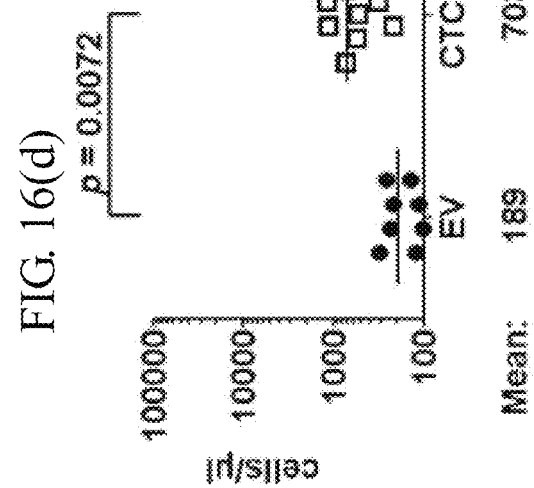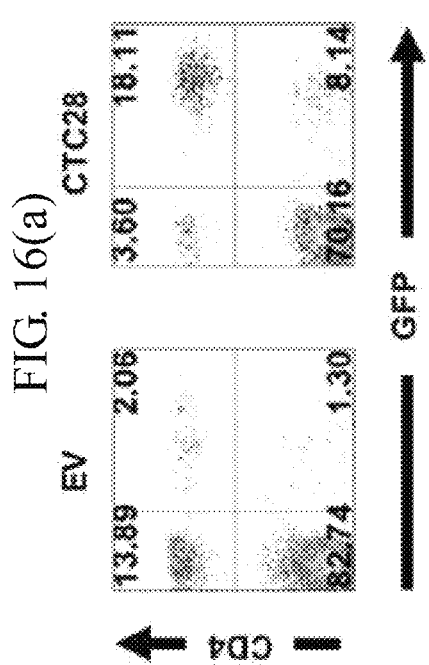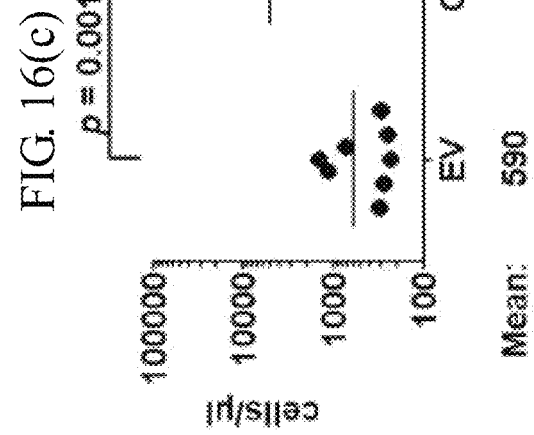

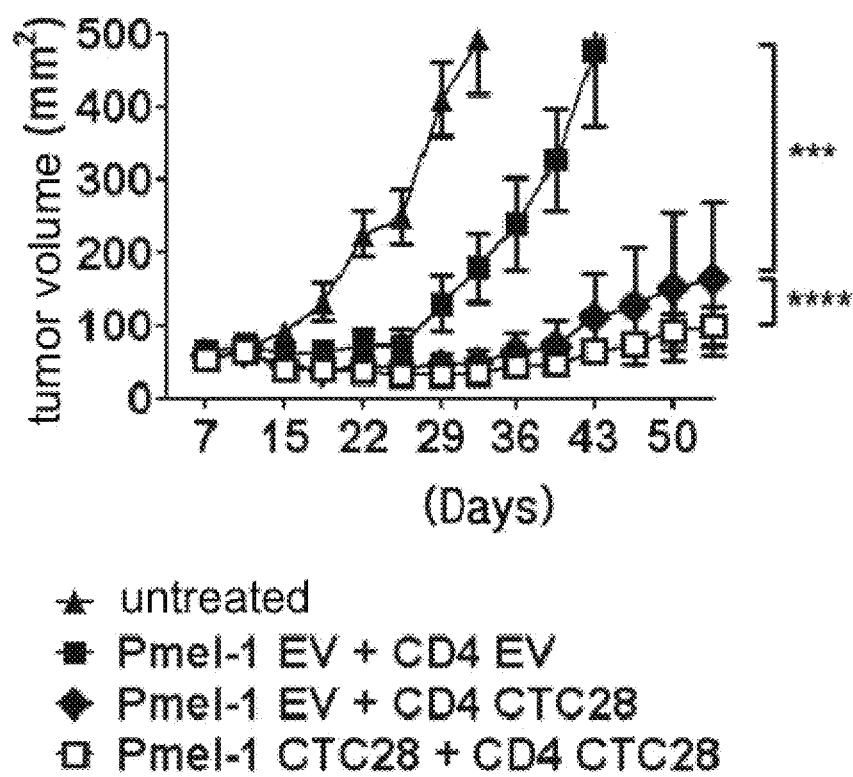

SEQUENCE LISTING

<160> NUMBER OF SEQ ID NOS: 10

<210> SEQ ID NO 1
<211> LENGTH: 223
<212> TYPE: PRT
<213> ORGANISM: Homo sapiens

<400> SEQUENCE: 1

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
    130                 135                 140

```
Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
                180                 185                 190

Arg Ser Pro Leu Thr Thr Gly Val Tyr Val Lys Met Pro Pro Thr Glu
                195                 200                 205

Pro Glu Cys Glu Lys Gln Phe Gln Pro Tyr Phe Ile Pro Ile Asn
    210                 215                 220
```

<210> SEQ ID NO 2
<211> LENGTH: 223
<212> TYPE: PRT
<213> ORGANISM: Mus musculus

<400> SEQUENCE: 2

```
Met Ala Cys Leu Gly Leu Arg Arg Tyr Lys Ala Gln Leu Gln Leu Pro
1               5                   10                  15

Ser Arg Thr Trp Pro Phe Val Ala Leu Leu Thr Leu Leu Phe Ile Pro
                20                  25                  30

Val Phe Ser Glu Ala Ile Gln Val Thr Gln Pro Ser Val Val Leu Ala
            35                  40                  45

Ser Ser His Gly Val Ala Ser Phe Pro Cys Glu Tyr Ser Pro Ser His
        50                  55                  60

Asn Thr Asp Glu Val Arg Val Thr Val Leu Arg Gln Thr Asn Asp Gln
65                  70                  75                  80

Met Thr Glu Val Cys Ala Thr Thr Phe Thr Glu Lys Asn Thr Val Gly
                85                  90                  95

Phe Leu Asp Tyr Pro Phe Cys Ser Gly Thr Phe Asn Glu Ser Arg Val
            100                 105                 110

Asn Leu Thr Ile Gln Gly Leu Arg Ala Val Asp Thr Gly Leu Tyr Leu
        115                 120                 125

Cys Lys Val Glu Leu Met Tyr Pro Pro Tyr Phe Val Gly Met Gly
130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Val Ala Val Ser Leu Gly Leu Phe Phe
                165                 170                 175

Tyr Ser Phe Leu Val Thr Ala Val Ser Leu Ser Lys Met Leu Lys Lys
                180                 185                 190

Arg Ser Pro Leu Thr Thr Gly Val Tyr Val Lys Met Pro Pro Thr Glu
                195                 200                 205

Pro Glu Cys Glu Lys Gln Phe Gln Pro Tyr Phe Ile Pro Ile Asn
    210                 215                 220
```

<210> SEQ ID NO 3
<211> LENGTH: 220
<212> TYPE: PRT
<213> ORGANISM: Homo sapiens

<400> SEQUENCE: 3

```
Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
                20                  25                  30
```

Asp Asn Ala Val Asn Leu Ser Cys Lys Tyr Ser Tyr Asn Leu Phe Ser
            35                  40                  45

Arg Glu Phe Arg Ala Ser Leu His Lys Gly Leu Asp Ser Ala Val Glu
 50                  55                  60

Val Cys Val Val Tyr Gly Asn Tyr Ser Gln Gln Leu Gln Val Tyr Ser
 65                  70                  75                  80

Lys Thr Gly Phe Asn Cys Asp Gly Lys Leu Gly Asn Glu Ser Val Thr
                 85                  90                  95

Phe Tyr Leu Gln Asn Leu Tyr Val Asn Gln Thr Asp Ile Tyr Phe Cys
             100                 105                 110

Lys Ile Glu Val Met Tyr Pro Pro Tyr Leu Asp Asn Glu Lys Ser
             115                 120                 125

Asn Gly Thr Ile Ile His Val Lys Gly Lys His Leu Cys Pro Ser Pro
         130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                 165                 170                 175

Phe Trp Val Arg Ser Lys Arg Ser Arg Leu Leu His Ser Asp Tyr Met
             180                 185                 190

Asn Met Thr Pro Arg Arg Pro Gly Pro Thr Arg Lys His Tyr Gln Pro
         195                 200                 205

Tyr Ala Pro Pro Arg Asp Phe Ala Ala Tyr Arg Ser
             210                 215                 220

<210> SEQ ID NO 4
<211> LENGTH: 218
<212> TYPE: PRT
<213> ORGANISM: Mus musculus

<400> SEQUENCE: 4

Met Thr Leu Arg Leu Leu Phe Leu Ala Leu Asn Phe Phe Ser Val Gln
 1               5                  10                  15

Val Thr Glu Asn Lys Ile Leu Val Lys Gln Ser Pro Leu Leu Val Val
             20                  25                  30

Asp Ser Asn Glu Val Ser Leu Ser Cys Arg Tyr Ser Tyr Asn Leu Leu
         35                  40                  45

Ala Lys Glu Phe Arg Ala Ser Leu Tyr Lys Gly Val Asn Ser Asp Val
 50                  55                  60

Glu Val Cys Val Gly Asn Gly Asn Phe Thr Tyr Gln Pro Gln Phe Arg
 65                  70                  75                  80

Ser Asn Ala Glu Phe Asn Cys Asp Gly Asp Phe Asp Asn Glu Thr Val
                 85                  90                  95

Thr Phe Arg Leu Trp Asn Leu His Val Asn His Thr Asp Ile Tyr Phe
             100                 105                 110

Cys Lys Ile Glu Phe Met Tyr Pro Pro Tyr Leu Asp Asn Glu Arg
             115                 120                 125

Ser Asn Gly Thr Ile Ile His Ile Lys Glu Lys His Leu Cys His Thr
         130                 135                 140

Gln Ser Ser Pro Lys Leu Phe Trp Ala Leu Val Val Val Ala Gly Val
145                 150                 155                 160

Leu Phe Cys Tyr Gly Leu Leu Val Thr Val Ala Leu Cys Val Ile Trp
                 165                 170                 175

Thr Asn Ser Arg Arg Asn Arg Leu Leu Gln Ser Asp Tyr Met Asn Met
             180                 185                 190

Thr Pro Arg Arg Pro Gly Leu Thr Arg Lys Pro Tyr Gln Pro Tyr Ala
            195                 200                 205

Pro Ala Arg Asp Phe Ala Ala Tyr Arg Pro
    210                 215

<210> SEQ ID NO 5
<211> LENGTH: 231
<212> TYPE: PRT
<213> ORGANISM: Homo sapiens

<400> SEQUENCE: 5

Met Ala Cys Leu Gly Phe Gln Arg His Lys Ala Gln Leu Asn Leu Ala
1               5                   10                  15

Thr Arg Thr Trp Pro Cys Thr Leu Leu Phe Leu Leu Phe Ile Pro
            20                  25                  30

Val Phe Cys Lys Ala Met His Val Ala Gln Pro Ala Val Val Leu Ala
            35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
                100                 105                 110

Asn Leu Thr Ile Gln Gly Leu Arg Ala Met Asp Thr Gly Leu Tyr Ile
            115                 120                 125

Cys Lys Val Glu Leu Met Tyr Pro Pro Pro Tyr Tyr Leu Gly Ile Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Val Arg Ser
                180                 185                 190

Lys Arg Ser Arg Leu Leu His Ser Asp Tyr Met Asn Met Thr Pro Arg
            195                 200                 205

Arg Pro Gly Pro Thr Arg Lys His Tyr Gln Pro Tyr Ala Pro Pro Arg
    210                 215                 220

Asp Phe Ala Ala Tyr Arg Ser
225                 230

<210> SEQ ID NO 6
<211> LENGTH: 231
<212> TYPE: PRT
<213> ORGANISM: Mus musculus

<400> SEQUENCE: 6

Met Ala Cys Leu Gly Leu Arg Arg Tyr Lys Ala Gln Leu Gln Leu Pro
1               5                   10                  15

Ser Arg Thr Trp Pro Phe Val Ala Leu Leu Thr Leu Leu Phe Ile Pro
            20                  25                  30

Val Phe Ser Glu Ala Ile Gln Val Thr Gln Pro Ser Val Val Leu Ala
            35                  40                  45

Ser Ser His Gly Val Ala Ser Phe Pro Cys Glu Tyr Ser Pro Ser His
    50                  55                  60

```
Asn Thr Asp Glu Val Arg Val Thr Val Leu Arg Gln Thr Asn Asp Gln
65                  70                  75                  80

Met Thr Glu Val Cys Ala Thr Thr Phe Thr Glu Lys Asn Thr Val Gly
                85                  90                  95

Phe Leu Asp Tyr Pro Phe Cys Ser Gly Thr Phe Asn Glu Ser Arg Val
            100                 105                 110

Asn Leu Thr Ile Gln Gly Leu Arg Ala Val Asp Thr Gly Leu Tyr Leu
        115                 120                 125

Cys Lys Val Glu Leu Met Tyr Pro Pro Tyr Phe Val Gly Met Gly
130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Val Ala Val Ser Leu Gly Leu Phe Phe
            165                 170                 175

Tyr Ser Phe Leu Val Thr Ala Val Ser Leu Ser Lys Met Thr Asn Ser
            180                 185                 190

Arg Arg Asn Arg Leu Leu Gln Ser Asp Tyr Met Asn Met Thr Pro Arg
            195                 200                 205

Arg Pro Gly Leu Thr Arg Lys Pro Tyr Gln Pro Tyr Ala Pro Ala Arg
210                 215                 220

Asp Phe Ala Ala Tyr Arg Pro
225                 230

<210> SEQ ID NO 7
<211> LENGTH: 229
<212> TYPE: PRT
<213> ORGANISM: Homo sapiens

<400> SEQUENCE: 7

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Tyr Tyr Leu Gly Ile Gly
130                 135                 140

Asn Gly Thr Gln Ile Tyr Val Ile Asp Pro Glu Pro Cys Pro Asp Ser
145                 150                 155                 160

Asp Phe Trp Val Leu Val Val Gly Val Leu Ala Cys Tyr Ser
            165                 170                 175

Leu Leu Val Thr Val Ala Phe Ile Ile Phe Trp Val Arg Ser Lys Arg
            180                 185                 190

Ser Arg Leu Leu His Ser Asp Tyr Met Asn Met Thr Pro Arg Arg Pro
            195                 200                 205
```

Gly Pro Thr Arg Lys His Tyr Gln Pro Tyr Ala Pro Arg Asp Phe
    210                 215                 220

Ala Ala Tyr Arg Ser
225

<210> SEQ ID NO 8
<211> LENGTH: 241
<212> TYPE: PRT
<213> ORGANISM: Mus musculus

<400> SEQUENCE: 8

Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45

Asn Ala Thr Phe Thr Cys Ser Leu Ser Asn Trp Ser Glu Asp Leu Met
    50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Pro Val Gln Asp Ala Arg Phe Gln
                85                  90                  95

Ile Ile Gln Leu Pro Asn Arg His Asp Phe His Met Asn Ile Leu Asp
            100                 105                 110

Thr Arg Arg Asn Asp Ser Gly Ile Tyr Leu Cys Gly Ala Ile Ser Leu
        115                 120                 125

His Pro Lys Ala Lys Ile Glu Glu Ser Pro Gly Ala Glu Leu Val Val
    130                 135                 140

Thr Glu Arg Ile Leu Glu Thr Ser Thr Arg Tyr Pro Ser Pro Ser Pro
145                 150                 155                 160

Lys Pro Glu Gly Arg Phe Gln Gly Met Val Ile Gly Ile Met Ser Ala
                165                 170                 175

Leu Val Gly Ile Pro Val Leu Leu Leu Leu Ala Trp Ala Leu Ala Val
            180                 185                 190

Phe Cys Ser Thr Ser Met Ser Thr Asn Ser Arg Arg Asn Arg Leu Leu
        195                 200                 205

Gln Ser Asp Tyr Met Asn Met Thr Pro Arg Arg Pro Gly Leu Thr Arg
    210                 215                 220

Lys Pro Tyr Gln Pro Tyr Ala Pro Ala Arg Asp Phe Ala Ala Tyr Arg
225                 230                 235                 240

Pro

<210> SEQ ID NO 9
<211> LENGTH: 567
<212> TYPE: DNA
<213> ORGANISM: murine

<400> SEQUENCE: 9
atggcttgtc ttggactccg gaggtacaaa gctcaactgc agctgccttc taggacttgg      60
ccttttgtag ccctgctcac tcttcttttc atcccagtct tctctgaagc catacaggtg     120
acccaacctt cagtggtgtt ggctagcagc catggtgtcg ccagctttcc atgtgaatat     180
tcaccatcac acaacactga tgaggtccgg gtgactgtgc tgcggcagac aaatgaccaa     240
atgactgagg tctgtgccac gacattcaca gagaagaata cagtgggctt cctagattac     300

```
ccettctgca gtggtacctt taatgaaagc agagtgaacc tcaccatcca aggactgaga    360
gctgttgaca cgggactgta cctctgcaag gtggaactca tgtacccacc gccatacttt    420
gtgggcatgg gcaacgggac gcagatttat gtcattgatc cagaaccatg cccggattct    480
gacttcctcc tttggatcct tgtcgcagtt agcttggggt tgtttttta cagtttcctg    540 gtcactgctg tttctttgag caagatg                                       567

<210> SEQ ID NO 10
<211> LENGTH: 129
<212> TYPE: DNA
<213> ORGANISM: murine

<400> SEQUENCE: 10
acaaatagta gaaggaacag actccttcaa agtgactaca tgaacatgac tccccggagg     60
cctgggctca ctcgaaagcc ttaccagccc tacgccctg ccagagactt tgcagcgtac    120
cgcccctga                                                            129
```

MUTANT CTLA4 GENE TRANSFECTED T CELL AND COMPOSITION INCLUDING SAME FOR ANTICANCER IMMUNOTHERAPY

CROSS REFERENCE TO RELATED APPLICATIONS AND CLAIM OF PRIORITY

This patent application claims benefit under 35 U.S.C. 119(e), 120, 121, or 365(c), and is a National Stage entry from International Application No. PCT/KR2012/008878, filed Oct. 26, 2012, which claims priority to Korean Patent Application Nos. 10-2011-0109729 filed Oct. 26, 2011 and 10-2011-0119603 filed Oct. 26, 2012, entire contents of which are incorporated herein by reference.

BACKGROUND

1. Field of the Invention

The present invention relates to a gene-modified T-cell for anticancer T-cell therapy and a composition for anticancer therapy comprising the same.

2. Description of the Related Art

The most fundamental and effective method for the treatment of cancer is surgical excision. However, it is not easy to remove residual tumor or metastatic foci by surgical excision alone, and thus various treatment methods such as chemotherapy, radiation therapy and the like have been used in combination with surgical excision. Despite the development of such treatment methods, the effective treatment of multiple metastases or other biochemical recurrence appearing after surgical excision is still difficult and remains as an important problem to be solved by medical science.

As a good method for the treatment of tumor foci or invisible micro-foci in various organs, immunotherapy based on the in vivo immune system has recently received attention. Robert Schreiber et al. reported a significant increase in the incidence of cancer in lymphocyte deficient mice or IFN-γ (effector cytokine)-knockout mice, suggesting that the development of cancer is inhibited by the immune system, particularly lymphocytes (Nature, 2001, vol. 410; 1107-1111). Particularly, there were many reports that specific antibodies or T-cells capable of recognizing tumor-associated antigens are present in vivo, suggesting that the applicability of anticancer immunotherapies is very high.

Therapies that have recently received the most attention among immunotherapies include cell therapies in which immune cells such as dendritic cells, natural killer cells (NK cells), or T-cells are injected directly into patients. Among them, T-cell therapy produces visible outcomes. The fundamental concept of T-cell therapy is that cancer antigen-specific T-cells are isolated from a patient, then cultured in vitro in large amounts, and are returned to the blood of the patient to attack cancer cells (Nat. Rev. Immunol. Vol. 6, 383). In other words, a small number of cancer-specific T-cells are cultured in vitro to increase the numbers thereof and are then used for cancer treatment.

In particular, the antigen specificity and tissue penetration ability of T-lymphocytes are expected to make it possible to effectively remove tumor foci present in various places. T-cells can penetrate tissue via extravasation to specifically kill antigen-expressing cells, and thus can penetrate various cancer tissues to remove cancer cells. Thus, in recent years, cancer therapies based on these anticancer T-cells have been actively developed.

Cell therapy based on T-cells has been attempted for the past 20-30 years by Dr. Steve Rosenberg et al. (NUH), named LAK (lymphokine-activated killer) or TIL (tumor-infiltrating lymphocyte) cell therapy, but the effectiveness thereof has been demonstrated in a limited number of cases. However, in recent years, it was reported that an attempt to deplete a patient's lymphocytes before injection of T-cells showed a response rate of 50%, including complete remission in metastatic melanoma patients, and thus this attempt was evaluated to make an important breakthrough for adoptive T cell transfer therapy (Science 2002, 298(5594):850-4; J. Clin. Oncol. 2005, 23(10):2346-57). It is presumed that lymphocyte depletion before injection of T-cells makes space for the proliferation of T-cells to be injected and has the effect of removing regulatory T-cells (i.e., an inhibitor of T-cell activator). This response rate is the highest among those in immunotherapies attempted to date and indicates the prospect of further development of this therapy.

By virtue of the success of cancer antigen-specific T-cell therapy, in recent years, there have been active studies on genetically engineered T-cell therapy in which isolated T-cells are genetically engineered to enhance the nature and efficacy thereof, and then injected into the patient. The concept of genetically engineered T-cell therapy is that cancer antigen-specific T-cells isolated from a patient are proliferated and then injected into the patient using a gene expression retrovirus after transduction. This concept is beyond the laboratory stage and is now in clinical trials in many cases.

However, in order to effectively remove cancer cells by cancer therapy using such cancer-specific T-cells, obstacles including the immune tolerance or suppression ability of cancer cells should be overcome. Development of cancer in normal mice or persons who have immunity, despite the tumor suppression ability of the immune system, means that cancer cells have resistance to the immune system, or immune evasion.

The reason why the immune tolerance of cancer cells is created has not yet been clearly established, and various hypotheses for the reason(s) have been presented, but the hypothesis that cancer cells induce tolerance to anticancer lymphocytes is valid. In other words, this hypothesis is that T-lymphocytes that can recognize and disrupt cancer cells are indeed present in the human body, but cancer cells or microenvironments surrounding cancer cells inactivate these anticancer T-cells.

Indeed, it was reported that cancer antigen-specific T-cells collected from melanoma patients secrete IFN-γ when they are stimulated with the cancer antigen Melan-A peptide, whereas cancer antigen-specific T-cells collected from cancer tissue or cancer tissue lymph nodes are in an inactivated state in which they cannot secrete IFN-γ even when they are stimulated with the antigen. This suggests that the peripheral blood of cancer cells has T-cells capable of recognizing and responding to cancer cells, but these T-cells are locally inactivated (e.g., tolerant) when they enter cancer tissue.

In other words, when T-cell tolerance to cancer cells is removed, the cancer cells can be effectively removed. Thus, it is an important prerequisite for anticancer immunotherapy to break immunological tolerance to cancer cells to activate anticancer lymphocytes. Various studies focused on the removal of T-cell tolerance to cancer cells have been conducted. Particularly, studies have been actively conducted to identify a receptor or protein involved in T-cell tolerance to cancer cells, and to remove or inhibit the function thereof or increase treatment effects using an antagonist or antibody against the receptor.

A receptor that is typically known to be involved in T-cell tolerance is Cytotoxic T-Lymphocyte-Associated Protein 4, or T-Lymphocyte Antigen 4 (CTLA4), also called CD152. CTLA4, a member of the superfamily of immunoglobulin, is expressed on the surface of T-cells and transduces an inhibitory signal to T-cells. The induction of tolerance by T-cell inactivation by the CTLA4 protein was confirmed by observation of severe lymphoproliferative disease and autoimmune disease in CTLA4-knockout mice.

CTLA4 has a sequence similar to that of the T-cell costimulatory protein CD28 and binds to CD80 and CD86, also called B7 of antigen-presenting cells, competitively with CD28. When it binds to B7, CTLA4 transduces an inhibitory signal, and CD28 transduces a stimulatory signal. In other words, when B7 binds to CTLA4, the activation of T-cells is inhibited, and when B7 binds to CD28, the activation of T-cells is induced.

Another protein that is involved in T-cell tolerance is PD1. It is known that PD1 is expressed on the surface of T-cells and binds to PD-L1 to inhibit the activation of T-cells. It is known that PD-L1, a family member having a structure similar to that of CD28, is expressed mainly on the surface of immune cells, including T-cells, B-cells, macrophages and dendritic cells, and is also expressed in some non-lymphoid cells such as cardiac vascular endothelial cells.

It is known that autoimmune disease naturally occurs in PD1-knockout mice and a native signal is transduced into T-cells by PD1 stimulation, suggesting that the inhibition of T-cell activity by the interaction between PD-L1 and PD1 is very important in immune tolerance.

However, in recent years, an increase in the expression in PD-L1 in many kinds of cancer tissues was observed (Nat. Med. 2002 August; 8(8):793-800), and it was reported that treatment with a blocking antibody against PD-L1 results in an increase in anticancer immunity (Proc. Natl. Acad. Sci. 17; 99(19):12293-7). This demonstrates that PD-L1 acts as an immune inhibitor on the surface of cancer cells.

Thus, it is expected that inhibition of receptors or proteins, such as CTLA4 or PD1, which are involved in T-cell immune tolerance can provide anticancer effects. Accordingly, studies on T-cell immunotherapy as a strategy for inhibiting the activity CTLA4 or PD1 using its antibody have been actively pursued.

In particular, it was clinically demonstrated that the anti-CTLA4 antibody Ipilimumab developed by Bristol-Myers Squib (BMS), or other similar companies, shows an anticancer effect against metastatic melanoma by inhibiting immune tolerance. Thus, this antibody was approved by the FDA in 2011 and is now marketed. Also, it is known that BMS and other companies are performing clinical trials for a complete humanized anti-PD1 antibody.

However, it is known that the use of anti-CTLA4 antibody or anti-PD1 antibody disrupts not only anticancer T-cells, but also T-cell tolerance to self-antigen, due to the systemic inhibition of CTLA4 or PD1, resulting in fatal side effects.

Thus, for actual clinical application of cancer antigen-specific T-cell therapy, there is an urgent need for the development of technology capable of inhibiting a T-cell tolerance signaling system for CTLA4 or PD1 only in anticancer T-cells.

Accordingly, the present inventors attempted to increase the activity of anticancer T-cells by competitively inhibiting the function of T-cell endogenous CTLA4 as a result of genetically engineering anti-cancer T-cells so as to express a CTLA decoy receptor that is a mutant CTLA lacking the intracellular inhibitory signaling domain of CTLA4. However, in the case of such genetically engineered T-cells, there was a problem in that the CTLA decoy receptor competitively inhibits the binding between CD28, that induces T-cell activation, and the ligand B7, ultimately resulting in the inhibition of T-cell activation, even though the CTLA decoy receptor may somewhat solve the T-cell tolerance problem, because an inhibitory signal is not transduced into cells even when the CTLA decoy receptor binds to the ligand B7.

Accordingly, the present inventors have designed an anticancer T-cell genetically engineered so as to express a CTLA4-CD28 chimera protein, which includes CTLA4 lacking its intracellular inhibitory signaling domain and the intracellular stimulatory signaling domain of CD28 protein, fused thereto (see FIG. 1). Using this designed anticancer T-cell, the present inventors have found that when a ligand binds to CTLA4, a T-cell inhibitory signal caused by the binding between CTLA4 and the ligand is converted to a stimulatory signal by the action of the intracellular stimulatory signaling domain of CD28 in the CTLA4-CD28 chimera protein, T-cell tolerance to cancer cells can be overcome, anticancer effects of the T-cell can be greatly enhanced by the activation thereof, and a side effect such as the development of autoimmune disease caused by the systemic inhibition of CTLA4 activity can be avoided, suggesting that the T-cell can be used for ideal T-cell immunotherapy. In addition, the present inventors have found that a T-cell genetically engineered so as to express a PD1-CD28 chimera protein that includes PD1 lacking its intracellular domain known to be involved in T-cell tolerance, similar to CTLA4 in the CTLA4-CD28 chimera protein, also increases T-cell activation, suggesting that the T-cell can be used for ideal T-cell immunotherapy.

SUMMARY

In one embodiment, provided is a fusion protein which includes a T-cell tolerance-inducing receptor lacking its intracellular signaling domain and the intracellular signaling domain of T-cell activating surface protein CD28, fused to the receptor, and a gene encoding the same.

In another embodiment, provided is a cancer antigen-specific T-cell transduced with a viral or non-viral carrier having the gene, and a production method thereof.

In still another embodiment, provided is a pharmaceutical composition for treating cancer, which includes the transduced T-cell.

In yet still another embodiment, provided is a method for treating cancer, which includes administering a pharmaceutically effective amount of the transduced T-cell to a subject suffering from cancer disease.

In one embodiment, provided is the use of the transduced T-cell for the preparation of a composition for treating cancer disease.

In one embodiment, provided is a CTLA4-CD28 chimera protein or a PD1-CD28 chimera protein, which is a fusion protein comprising CTLA4 or PD1 lacking its intracellular inhibitory signaling domain and the intracellular stimulatory signaling domain of the CD28 protein, which is fused to the CTLA4 or PD1, and a gene encoding the fusion protein.

In one embodiment, provided is a cancer antigen-specific T-cell transduced with a non-viral carrier having the gene, and a production method thereof.

In another embodiment, provided is a pharmaceutical composition for treating cancer, which includes the transduced T-cell.

In yet another embodiment, provided is a method for treating cancer, which includes administering a pharmaceutically effective amount of the transduced T-cell to a subject suffering from cancer disease.

In yet still another embodiment, provided is the use of the transduced T-cell for the preparation of a composition for treating cancer disease.

A T-cell transduced with a CTLA4-CD28 chimera gene or PD1-CD28 chimera gene as disclosed may solve the problem associated with the inhibition of treatment effects caused by the immune tolerance of cancer cells, and may maximize the anticancer effects by inducing the signaling of CD28 to induce the activation of T-cells.

In addition, the transduced T-cell as disclosed may inhibit the activity of CTLA4 or PD1 in cancer cells, thereby minimizing side effects such as the development of autoimmune disease, which occurs when a non-specific CTLA4 or PD1 antagonist, such as existing anti-CTLA4 antibody, is used.

Thus, in one embodiment, a pharmaceutical composition for treating cancer, which includes a T-cell transduced with the CTLA4-CD28 chimera gene or the PD1-CD28 chimera gene disclosed herein may be useful for T-cell immunotherapy having significantly excellent effects on the treatment of cancer compared to existing methods.

CTdc: CTLA4 decoy receptor; and
CTC28: CTLA4-CD28 chimera protein.
(CTdc and CTC28 are applied to other figures in the same manner).

Figure 2A:
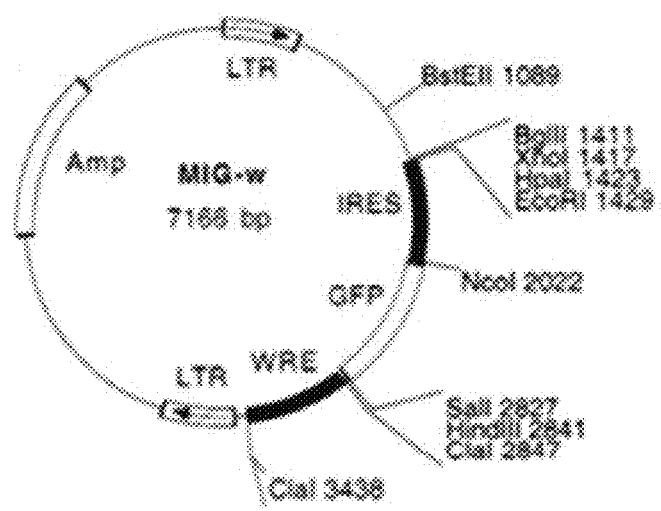
Figure 2B:
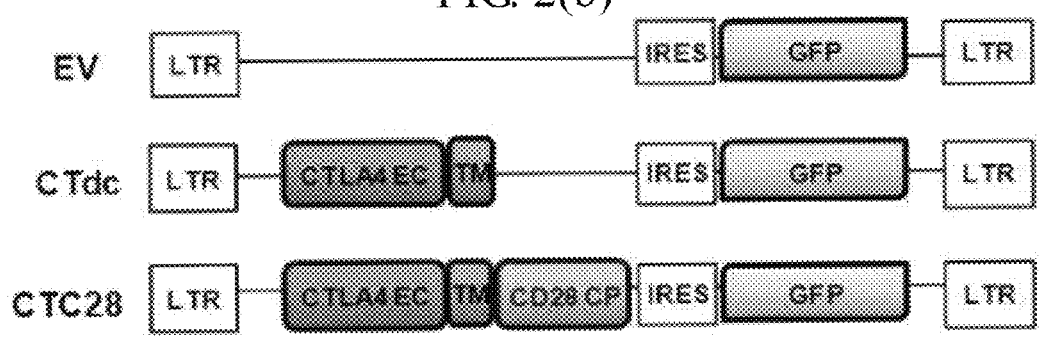

FIGS. 2(a) and 2(b) show a gene structure for expression of CTLA4-CD28 and a restriction map of a plasmid. FIG. 2(a) shows a restriction map of a pMIG-w retroviral vector, and FIG. 2(b) shows the structure of a CTLA4-CD28 retroviral gene.

CTLA4 EC: the extracellular domain of CTLA4;
TM: transmembrane domain;
CD28 CP: the intracellular domain of CD28; and
EV: a retroviral empty vector containing no CTLA4-CD28.
(CTLA4 EC, TM, CD28 CP, and EV are applied to other figures in the same manner).

Figure 3A:
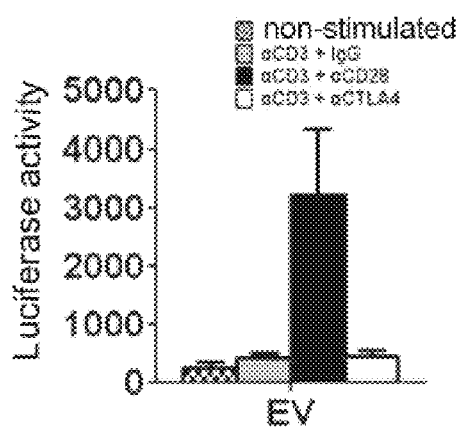
Figure 3B:
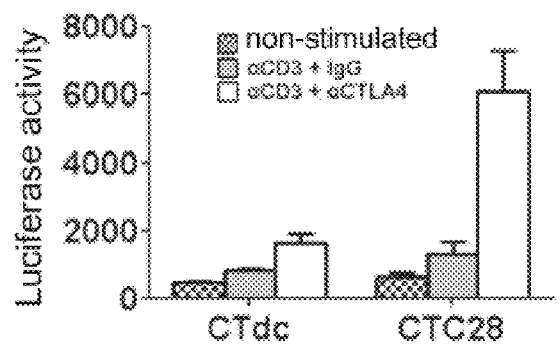
Figure 3C:
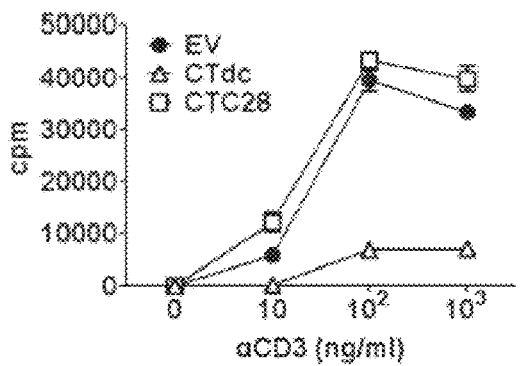
Figure 3D:
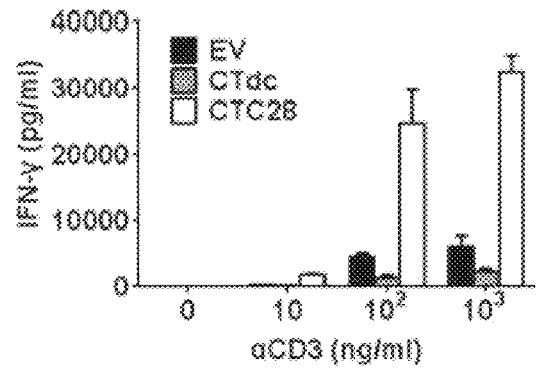

FIGS. 3(a) to 3(d) show the cell division and IFN-γ secretion of T-cells transduced with one embodiment of a CLTA4-CD28 chimera gene. FIG. 3(a) shows luciferase activity in T-cells which were not genetically engineered; FIG. 3(b) shows luciferase activity in T-cells transduced with CTdc or CTC28; FIG. 3(c) shows cell division of T-cells transduced with CTdc or CTC28; and FIG. 3(d) shows IFN-Y secretion of T-cells transduced with CTdc or CTC28.

Figure 4A:
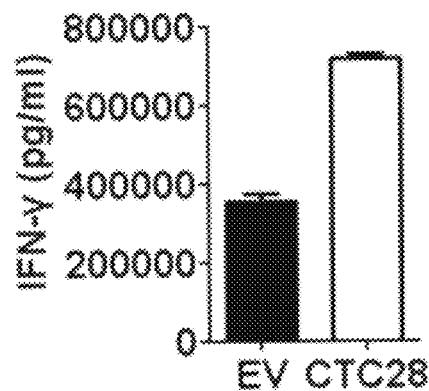
Figure 4B:
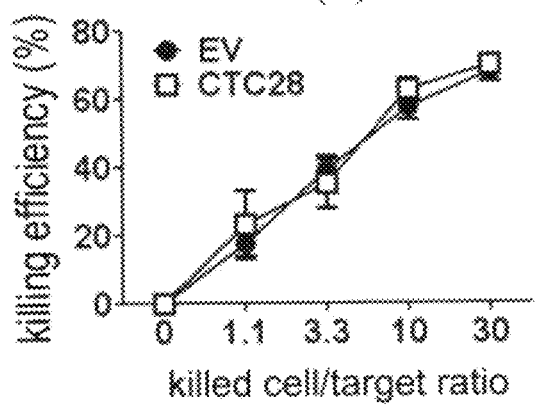
Figure 4C:
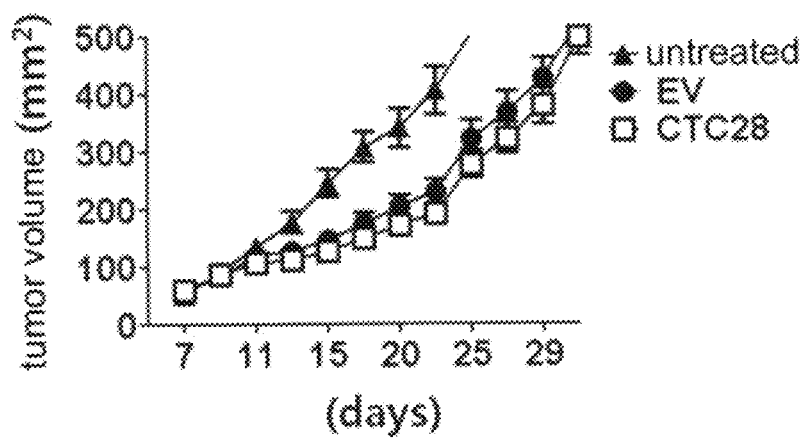

FIGS. 4(a) to 4(c) show the IFN-γ secretion, cancer-killing ability, and tumor treatment effect of T-cells transduced with one embodiment of a CLTA4-CD28 chimera gene. FIG. 4(a) shows IFN-γ secretion of T-cells transduced with CTC28; FIG. 4(b) shows cancer cell-killing ability of T-cells transduced with CTC28; and FIG. 4(c) shows tumor treatment effect of T-cells transduced with CTC28.

Figure 5A:
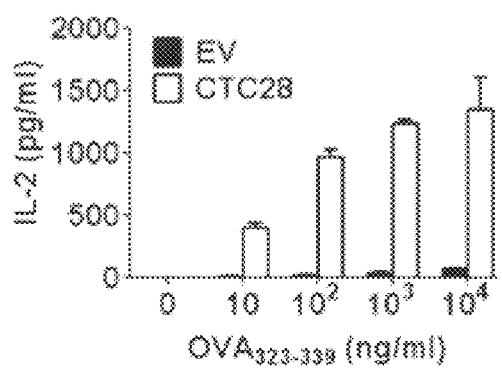
Figure 5B:
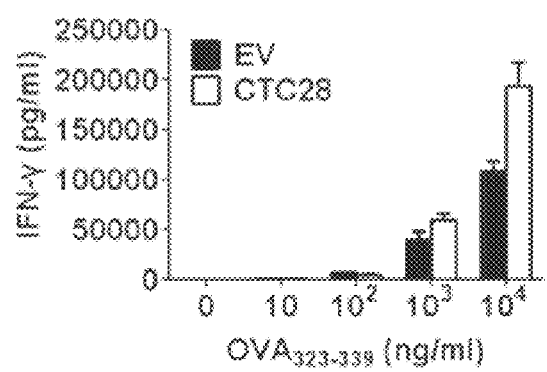
Figure 5C:
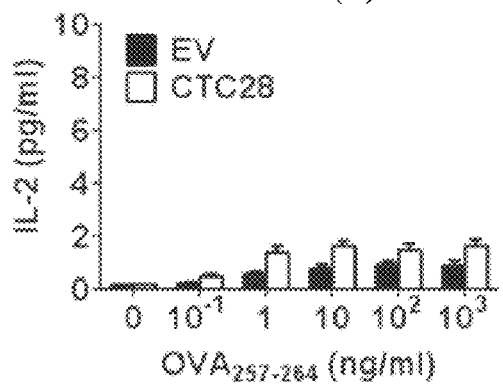
Figure 5D:
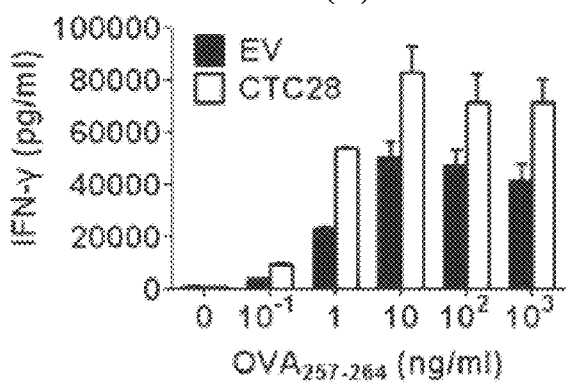

FIGS. 5(a) to 5(d) show the response of CLTA4-CD28 chimera gene-transduced T-cells to antigen during cell culture. FIG. 5(a) shows IL-2 secretion of CD4 OT-II cells; FIG. 5(b) shows IFN-γ secretion of CD4 OT-II cells; FIG. 5(c) shows IL-2 secretion of CD8 OT-I cells; and FIG. 5(d) shows IFN-γ secretion of CD8 OT-I cells.

Figure 6:
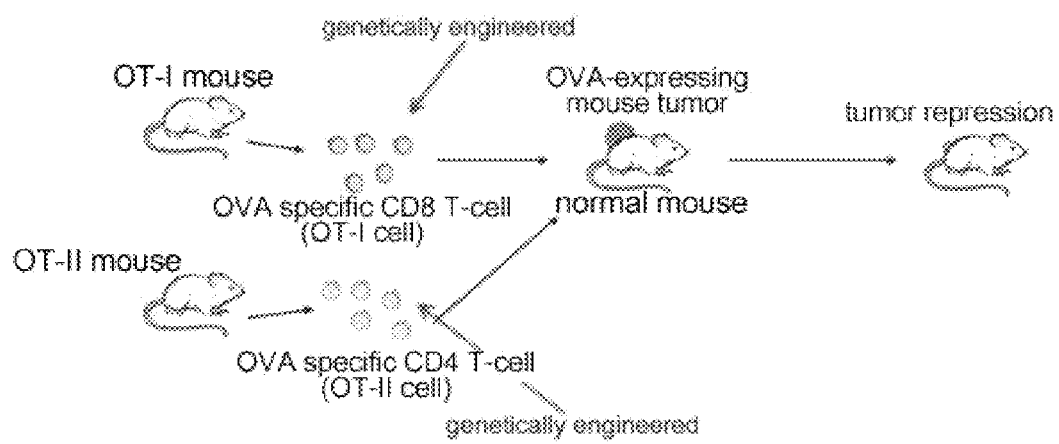

FIG. 6 shows a combination therapy model using genetically engineered CD4 and CD8 T-cells.

Figure 7:
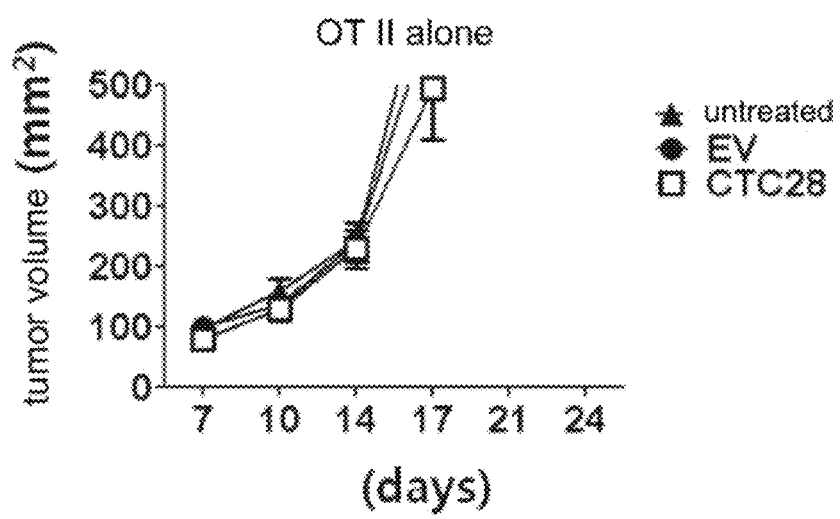

FIG. 7 shows the effect of administration of OT-II T-cells alone against an E.G7 tumor.

Figure 8A:
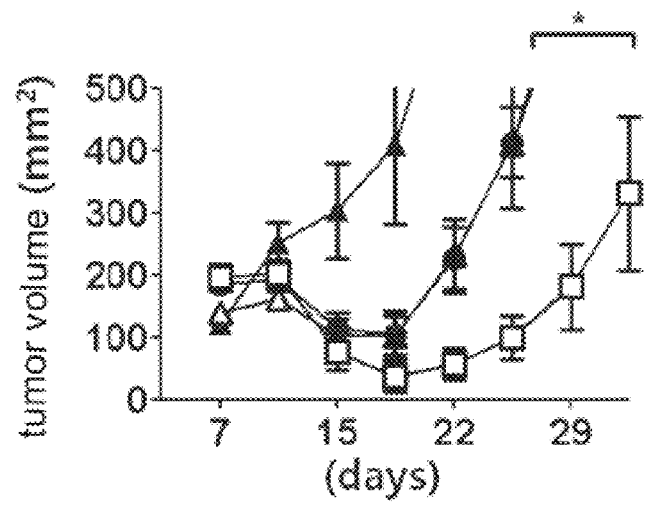
Figure 8B:
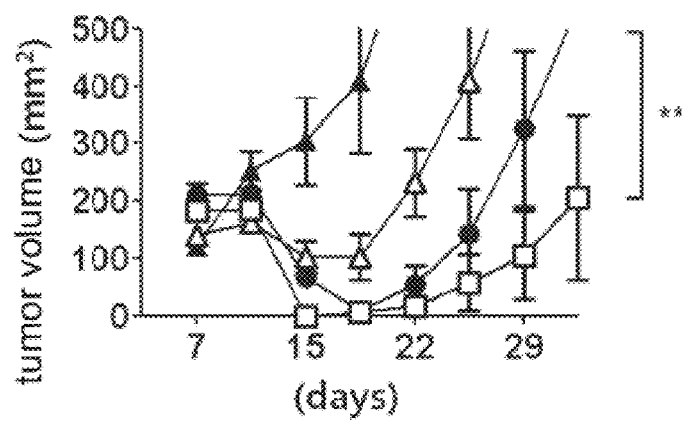
Figure 8C:
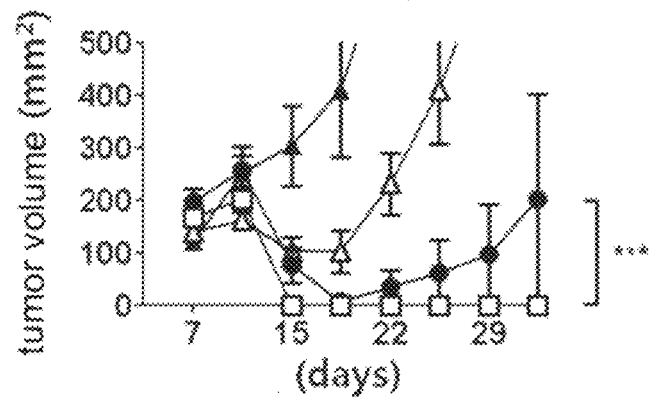

FIGS. 8(a) to 8(c) show the effect of administration of a combination of OT-I T-cells and OT-II T-cells transduced with one embodiment of a CTLA4-CD28 chimera gene, against an E.G7 tumor. (▲: untreated; Δ: use of OT-I alone; •: OT-I+OT-II, □: OT-I+OT-II CTC28). In FIG. 8(a), the ratio of OT-I T-cell:OT-II T-cell=2:0.5; in FIG. 8(b), the ratio of OT-I T-cell:OT-II T-cell=2:1; and in FIG. 8(c) the ratio of OT-I T-cell:OT-II T-cell=2:2.

Figure 9:
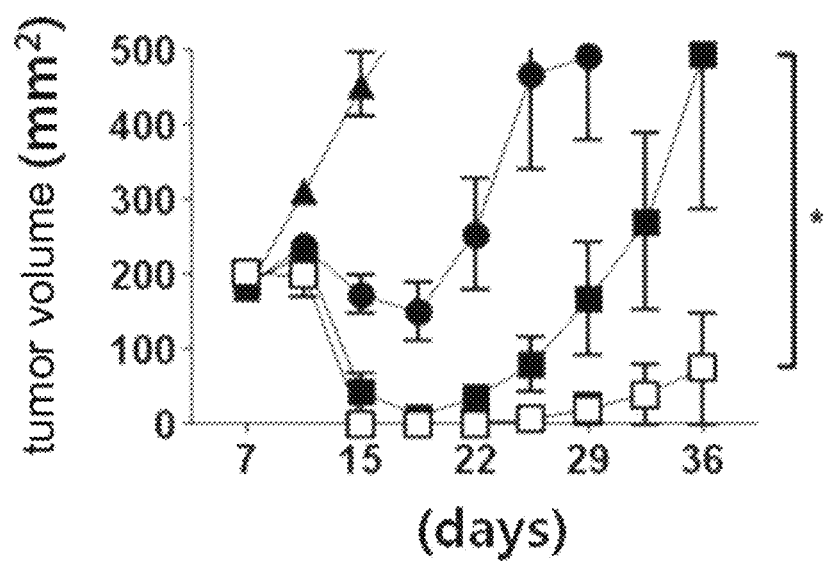

FIG. 9 shows the effect of co-transduction of OT-II and OT-I T-cells on tumor treatment.
(▲: untreated; ■: OT-I+OT-II; •: OT-I+OT-II CTC28; □: OT-I CTC28+OT-II CTC28).

Figure 10A:
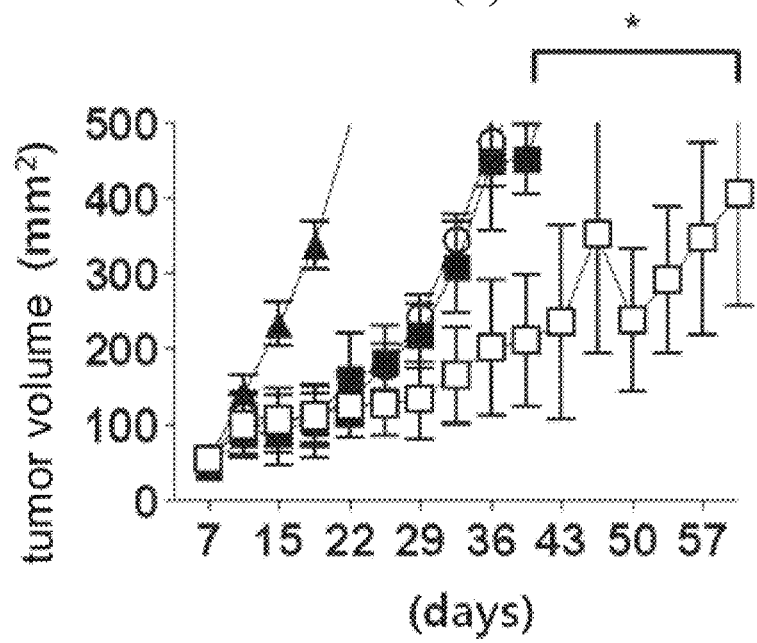
Figure 10B:
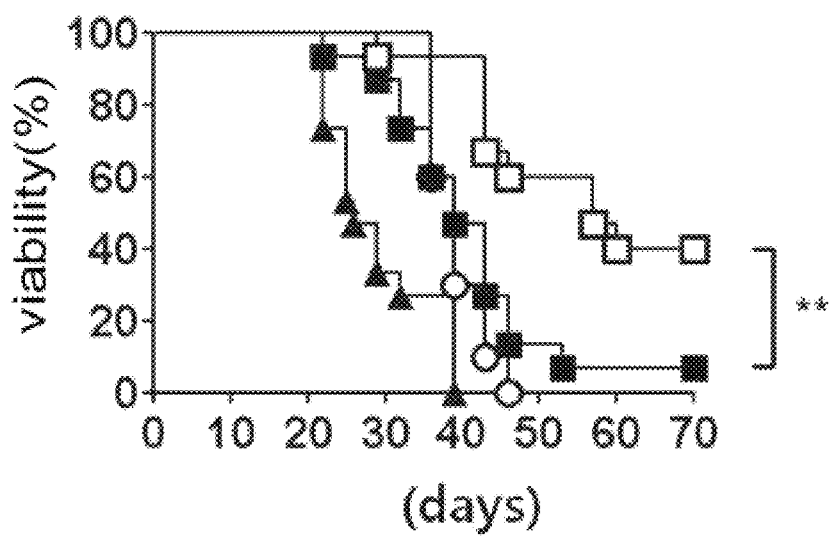

FIGS. 10(a) and 10(b) show the anti-melanoma effect of a therapy using a combination of genetically engineered CD4 and CD8 T-cells.
(▲: untreated; ○: Pmel-1 EV; ■: Pmel-1 EV+CD4 EV; □: Pmel-1 CTC28+CD4 CTC28). FIG. 10(a) shows change in tumor volume; and FIG. 10(b) shows change in viability.

Figure 11:
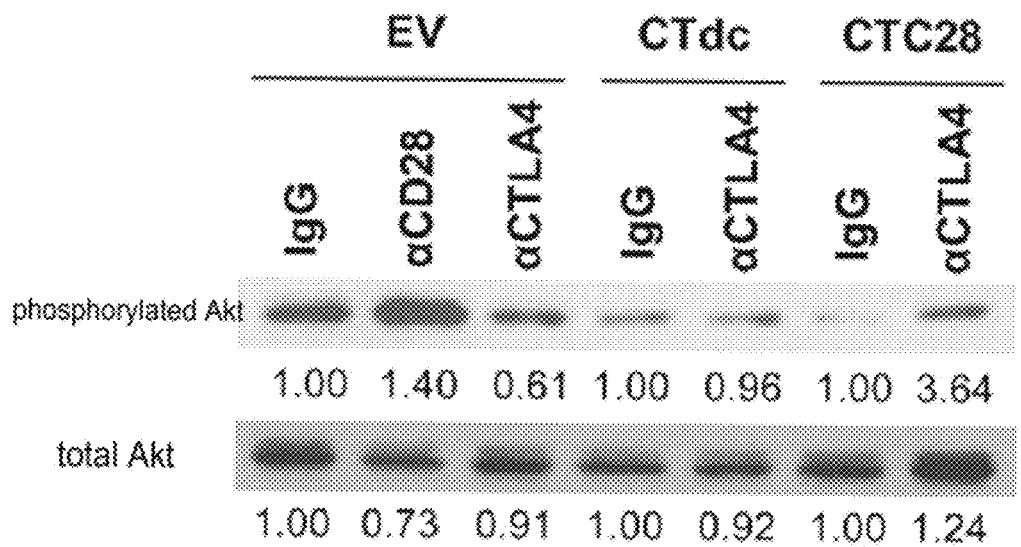

FIG. 11 shows the Akt phosphorylation of T-cells transduced with one embodiment of a CTLA4-CD28 chimera gene.

Figure 12:
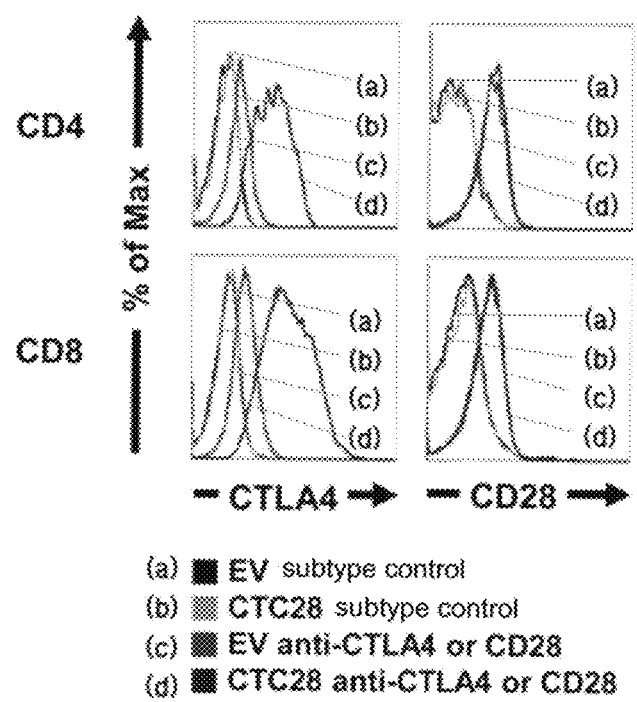

FIG. 12 shows the results of analyzing T-cells, transduced with gene structures for expression of one embodiment of CTLA4-CD28, using a flow cytometer.

Figure 13:
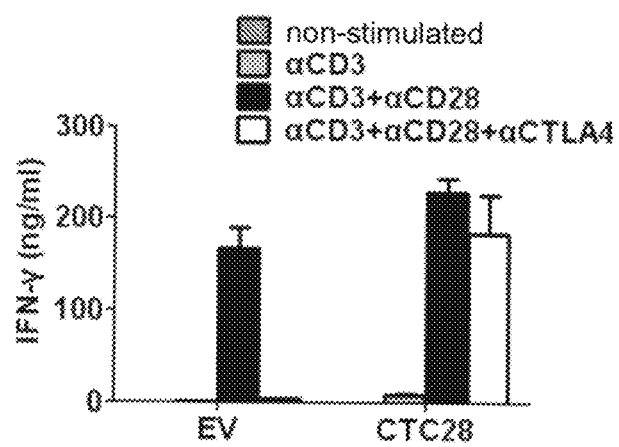

FIG. 13 shows the IFN-γ secretion of T-cells transduced with one embodiment of a CTLA4-CD28 chimera gene when the cells are stimulated with each receptor.

Figure 14:
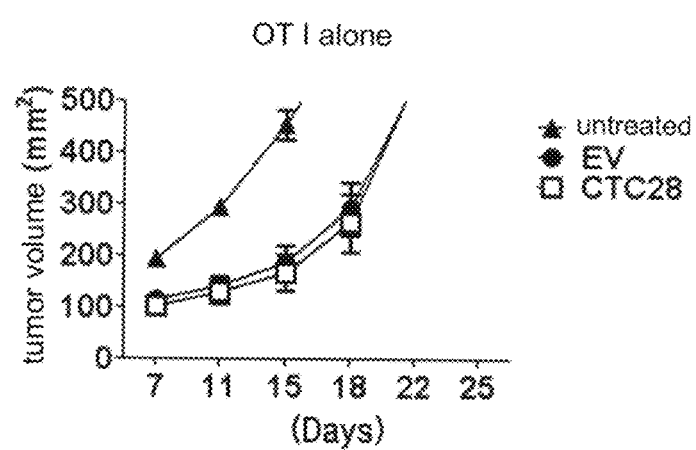

FIG. 14 shows the effect of administration of OT-I T-cells alone against an E.G7 tumor.

Figure 15A:
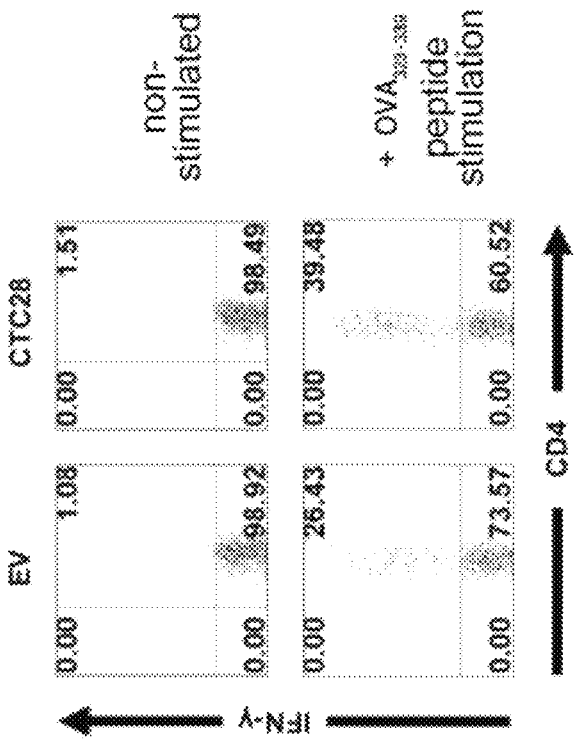
Figure 15B:
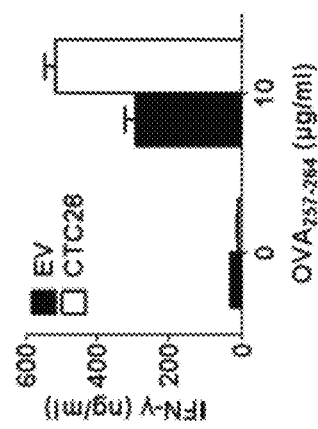
Figure 15C:
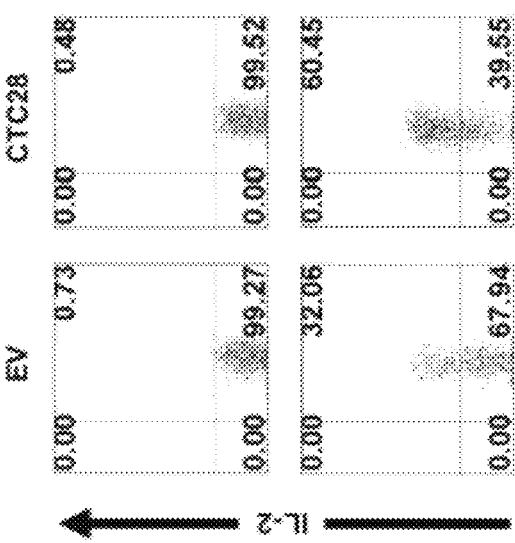
Figure 15D:
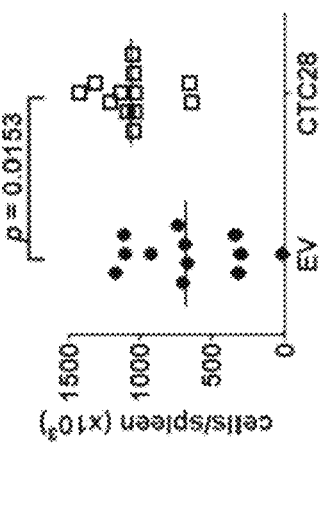

FIGS. 15(a) to 15(d) show the number and response-to-antigen of transduced OT-I and OT-II T-cells in the spleen of E.G7 tumor-bearing mice after administration of these T-cells to the mice. FIGS. 15(a) and 15(b) show results of analyzing the response of transduced OT-I and OT-II T-cells to antigen during cell culture using a flow cytometer; FIG. 15(c) show results of analyzing the proliferation of transduced OT-II T-cells in mice using a flow cytometer; and FIG. 15(d) shows IFN-γ secretion of transduced OT-I T-cells after the response of the cells to antigen during cell culture.

FIGS. 16(a) to 16(d) show the proliferation of genetically engineered CD4 and CD8 T-cells in blood, which indicates the anti-melanoma effect of a combination of the cells. FIG. 16(a) shows results of analyzing the ratio of CD4 T-cells in blood cells using a flow cytometer; FIG. 16(b) shows results of analyzing the ratio of Pmel-1 T-cells in blood cells using a flow cytometer; FIG. 16(c) shows results of analyzing the number of CD4 T-cells in blood cells using a flow cytometer (•: CD4 EV; □: CD4 CTC28); and FIG. 16(d) shows results of analyzing the number of Pmel-1 T-cells in blood cells using a flow cytometer (•: Pmel-1 EV; □: Pmel-1 CTC28).

FIG. 17 shows the anti-melanoma effect of a combination of genetically engineered CD4 and CD8 T-cells.
(▲: untreated; ■: Pmel-1 EV+CD4 EV; ♦: Pmel-1 EV+CD4 CTC28; □: Pmel-1 CTC28+CD4 CTC28).

Figure 18:
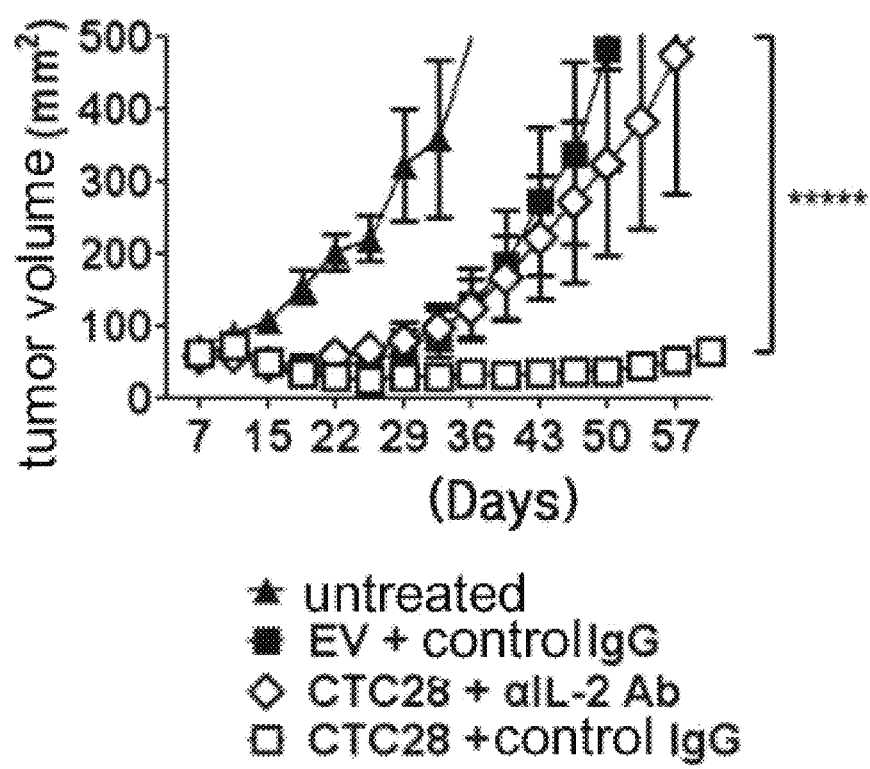

FIG. 18 shows the anti-melanoma effect of IL-2 in a combination of genetically engineered CD4 and CD8 T-cells.
(▲: untreated; ■: CTC28+control IgG antibody; ◊: CTC28+anti-IL-2 antibody; □: CTC28+control IgG antibody).

DETAILED DESCRIPTION

Hereinafter, the terms used in the disclosure will be described in detail.

As used herein, the term "extracellular domain" means a domain exposed to an extracellular region so as to be able to bind to a ligand or the like; the term "transmembrane domain" refers to the domain of CTLA4, CD28, or the like, which is located on the cell membrane; and term "intracellular domain" refers to a domain that is located in cells and transduces a signal, caused by the binding between an extracellular domain and a ligand, into cells.

The intracellular domain can be divided, according to the nature of a signal, into an inhibitory signaling domain and an activation signaling domain.

As used herein, the term "anticancer" includes prevention and treatment. Herein, the term "prevention" refers to all actions that inhibit cancer or delay the development of cancer by administering a composition having a cancer antigen-specific T-cell transduced with one embodiment of a CTLA4-CD28 chimera gene or one embodiment of a PD1-CD28 chimera gene as disclosed; and the term "treatment" refers to all actions that alleviate or beneficially change cancer by administering a composition comprising a cancer antigen-specific T-cell transduced with one embodiment of a CTLA4-CD28 chimera gene or one embodiment of a PD1-CD28 chimera gene as disclosed.

Hereinafter, the present invention will be described in detail.

Provided is a fusion protein having a T-cell surface tolerance-inducing receptor lacking its intracellular signaling domain and the intracellular signaling domain of T-cell-activating surface protein CD28, fused to the receptor.

The T-cell surface tolerance-inducing receptor and the T-cell-activating surface protein CD28 are, without limitation, fused to each other by the transmembrane domain of CD28.

The T-cell surface tolerance-inducing receptor may be Cytotoxic T lymphocyte associated antigen4 (CTLA4) or PD1.

The fusion protein has either the extracellular domain of CTLA4, the transmembrane domain of CTLA4 and the intracellular domain of CD28, or the extracellular domain of CTLA4, the transmembrane domain of CD28 and the intracellular domain of CD28, without limitation.

The fusion protein has either the extracellular domain of PD1, the transmembrane domain of PD1 and the extracellular domain of CD28, or the extracellular domain of PD-1, the transmembrane domain of CD28 and the intracellular domain of CD28, without limitation.

The CTLA4 has an amino acid sequence of SEQ ID NO: 1, which is of human origin, or an amino acid sequence of SEQ ID NO: 2, which is of murine origin.

In the amino acid sequences of SEQ ID NOs: 1 and 2, the region of amino acid residues 1-161 corresponds to the extracellular domain that binds to a ligand such as B7; the region of amino acid residues 162-189 corresponds to the transmembrane domain; and the region of amino acid residues 190-223 corresponds to the intracellular domain.

The CD28 has an amino acid sequence of SEQ ID NO: 3, which is of human origin, or an amino acid sequence of SEQ ID NO: 4, which is of murine origin.

In the amino acid sequences of SEQ ID NO: 3, the region of amino acid residues 1-152 corresponds to the extracellular domain that binds to a ligand such as B7; the region of amino acid residues 153-178 corresponds to the transmembrane domain; and the region of amino acid residues 179-220 corresponds to the intracellular domain. In the amino acid sequences of SEQ ID NO: 4, the region of amino acid residues 1-150 corresponds to the extracellular domain that binds to a ligand such as B7; the region of amino acid residues 151-176 corresponds to the transmembrane domain; and the region of amino acid residues 177-218 corresponds to the intracellular domain.

In addition, when the transmembrane domain of CTLA4 is used in the CLTA4-CD28 chimera protein, the scope of the present invention encompasses the case in which a portion of the sequence of the intracellular domain of CTLA4 is further included in the extracellular domain and transmembrane domain in a range that does not impair the intracellular inhibitory signal of CTLA4, or the case in which a portion of the sequence of the transmembrane domain of CD28 is further included in the extracellular domain of CD28. Also, when the transmembrane domain of CD28 is used in the CLTA4-CD28 chimera protein, the scope of the present invention encompasses the case in which a portion of the sequence of the extracellular domain is further included in the intracellular domain and transmembrane domain of CD28 in a range that does not impair the binding between CTLA4 and a ligand, or the case in which a portion of the sequence of the transmembrane domain of CTLA4 is further included in the extracellular domain of CTLA4.

An example of the CTLA4-CD28 chimera protein may have any one amino acid sequence of SEQ ID NO: 5 to SEQ ID NO: 7.

The fusion protein composed of the extracellular domain of CTLA4, the transmembrane domain of CTLA4, and the intracellular domain of CD28 has an amino acid sequence of SEQ ID NO: 5 or 6, without limitation.

The fusion protein composed of the extracellular domain of CTLA4, the transmembrane domain of CD28, and the intracellular domain of CD28 has an amino acid sequence of SEQ ID NO: 7, without limitation.

The fusion protein composed of either the extracellular domain of PD1, the transmembrane domain of PD1, and the intracellular domain of CD28, or the extracellular domain of PD1, the transmembrane domain of CD28, and the intracellular domain of CD28 has an amino acid sequence of SEQ ID NO: 8, without limitation.

TABLE 1

Amino acid sequences

| No. | Seq Nature | Sequence |
|---|---|---|
| 1 | CTLA4 Homo sapiens | MACLGFQRHK AQLNLATRTW PCTLLFFLLF IPVFCKAMHV AQPAVVLASS RGIASFVCEY ASPGKATEVR VTVLRQADSQ VTEVCAATYM MGNELTFLDD SICTGTSSGN QVNLTIQGLR AMDTGLYICK VELMYPPPYY LGIGNGTQIY VIDPEPCPDS DFLLWILAAV SSGLFFYSFL LTAVSLSKML KKRSPLTTGV YVKMPPTEPE CEKQFQPYFI PIN (SEQ ID NO: 1) |
| 2 | CTLA4 Mus musculus | MACLGLRRYK AQLQLPSRTW PFVALLTLLF IPVFSEAIQV TQPSVVLASS HGVASFPCEY SPSHNTDEVR VTVLRQTNDQ MTEVCATTFT EKNTVGFLDY PFCSGTFNES RVNLTIQGLR AVDTGLYLCK VELMYPPPYF VGMGNGTQIY |

TABLE 1-continued

Amino acid sequences

| No. Seq | Nature | Sequence |
|---|---|---|
| | | VIDPEPCPDS DFLLWILVAV SLGLFFYSFL VTAVSLSKML KKRSPLTTGV YVKMPPTEPE CEKQFQPYFI PIN (SEQ ID NO: 2) |
| 3 | CD28 Homo sapiens | MLRLLLALNL FPSIQVTGNK ILVKQSPMLV AYDNAVNLSC KYSYNLFSRE FRASLHKGLD SAVEVCVVYG NYSQQLQVYS KTGFNCDGKL GNESVTFYLQ NLYVNQTDIY FCKIEVMYPP PYLDNEKSNG TIIHVKGKHL CPSPLFPGPS KPFWVLVVVG GVLACYSLLV TVAFIIFWVR SKRSRLLHSD YMNMTPRRPG PTRKHYQPYA PPRDFAAYRS (SEQ ID NO: 3) |
| 4 | CD28 Mus musculus | MTLRLLFLAL NFFSVQVTEN KILVKQSPLL VVDSNEVSLS CRYSYNLLAK EFRASLYKGV NSDVEVCVGN GNFTYQPQFR SNAEFNCDGD FDNETVTFRL WNLHVNHTDI YFCKIEFMYP PPYLDNERSN GTIIHIKEKH LCHTQSSPKL FWALVVVAGV LFCYGLLVTV ALCVIWTNSR RNRLLQSDYM NMTPRRPGLT RKPYQPYAPA RDFAAYRP (SEQ ID NO: 4) |
| 5 | CTLA-CD28 Chimera Homo sapiens | MACLGFQRHK AQLNLATRTW PCTLLFFLLF IPVFCKAMHV AQPAVVLASS RGIASFVCEY ASPGKATEVR VTVLRQADSQ VTEVCAATYM MGNELTFLDD SICTGTSSGN QVNLTIQGLR AMDTGLYICK VELMYPPPYY LGIGNGTQIY VIDPEPCPDS DFLLWILAAV SSGLFFYSFL LTAVSLSKMV RSKRSRLLHS DYMNMTPRRP GPTRKHYQPY APPRDFAAYR S (SEQ ID NO: 5) |
| 6 | CTLA-CD28 Chimera Mus musculus | MACLGLRRYK AQLQLPSRTW PFVALLTLLF IPVFSEAIQV TQPSVVLASS HGVASFPCEY SPSHNTDEVR VTVLRQTNDQ MTEVCATTFT EKNTVGFLDY PFCSGTFNES RVNLTIQGLR AVDTGLYLCK VELMYPPPYF VGMGNGTQIY VIDPEPCPDS DFLLWILVAV SLGLFFYSPL VTAVSLSKMT NSRRNRLLQS DYMNMTPRRP GLTRKPYQPY APARDFAAYR P (SEQ ID NO: 6) |
| 7 | CTLA-CD28 Chimera Homo sapiens | MACLGFQRHK AQLNLATRTW PCTLLFFLLF IPVFCKAMHV AQPAVVLASS RGIASFVCEY ASPGKATEVR VTVLRQADSQ VTEVCAATYM MGNELTFLDD SICTGTSSGN QVNLTIQGLR AMDTGLYICK VELMYPPPYY LGIGNGTQIY VIDPEPCPDS DFWVLVVVGG VLACYSLLVT VAFIIFWVRS KRSRLLHSDY MNMTPRRPGP TRKHYQPYAP PRDFAAYRS (SEQ ID NO: 7) |
| 8 | PD1-CD28 Chimera Mus musculus | MWVRQVPWSF TWAVLQLSWQ SGWLLEVPNG PWRSLTFYPA WLTVSEGANA TFTCSLSNWS EDLMLNWNRL SPSNQTEKQA AFCNGLSQPV QDARFQIIQL TSTRYPSPSP KPEGRFQGMV IGIMSALVGI PVLLLLAWAL AVFCSTSMST NSRRNLLQS DYMNMTPRRP GLTRKPYQPY APARDFAAYR P (SEQ ID NO: 8) |

In one embodiment, provided is a gene encoding one embodiment of the fusion protein.

The gene encoding the extracellular domain of CTLA4 and the membrane domain of CTLA4 has a nucleotide sequence of SEQ ID NO: 9, and the gene encoding the intracellular domain of CD28 has a nucleotide sequence of SEQ ID NO: 10, without limitation.

In one embodiment, provided is a viral or non-viral carrier having a gene encoding one embodiment of the fusion protein.

The viral or non-viral carrier that is used may be any carrier that can be transfected into an animal cell, including a T-cell.

Examples of viral carriers include, without limitation, a retrovirus, lentivirus, adenovirus and adeno-associated virus.

The non-viral virus that may be used herein is a transposon system (Hackett et al, U.S. Pat. No. 6,489,458) or the like, without limitation.

The present invention also provides a T-cell transduced with a viral or non-viral carrier having a gene encoding one embodiment of the fusion protein disclosed herein.

Examples of the T-cell include, but are not limited to, a cancer antigen-specific T-cell, a T-cell transformed with a chimera antigen receptor (CAR) gene, a cancer antigen-specific CD4 T-cell (helper T-cell) and a CD8 T-cell (cytotoxic T-cell).

As used herein, the term "chimeric antigen receptor" refers to a fusion protein of the membrane or intracellular signaling region of T-cell activating proteins (e.g., CD3-zeta chain, CD28, 41BBL, Ox40, ICOS, high-affinity receptor for IgE (FcεRI) and other T-cell activating proteins) and the antigen-binding site (i.e., single-chain Fv fragment) of a cancer antigen-specific antibody.

Examples of the cancer antigen-specific T-cell that is used in the present invention include, but are not limited to: cells obtained by in vitro culture of T-cells (e.g., tumor infiltrating lymphocytes) isolated from the cancer tissue of patients; TCR gene-modified T cells (Science 2006; 314(5796):126-9) obtained by transducing whole T-cells, isolated from the peripheral blood of patients, with a viral vector (such as a retrovirus) cloned with a receptor that specifically recognizes cancer antigen, that is, a cancer antigen-specific T-cell receptor (TCR) gene; and CAR-transduced T-cells (Blood 2010; 116(7):1035-1044) transduced with Chimeric Antigen Receptor (CAR) (J. Clin. Invest. 117:1466-1476 (2007) obtained by replacing the extracellular domain of T-cell receptor (TCR) with cancer antigen-specific antibody.

In the present invention, examples of the antigen that can be recognized specifically by the cancer antigen-specific T-cell include, but are not limited to, MUC1, CD19, HER2, EGFR, CD20, CEA, PSMA, GD2, folate receptor, IL-13Rα2, Lewis-Y antigen, NY-ESO-1, MART-1, gp100, tyrosinase, tyrosinase-related proteins, MAGE, WT-1 and the like. In addition, antigens that are expressed specifically in other cancers may also be used for T-cell immunotherapy according to the present invention, as long as they are suitable for the purpose of the present invention.

Figure 1:
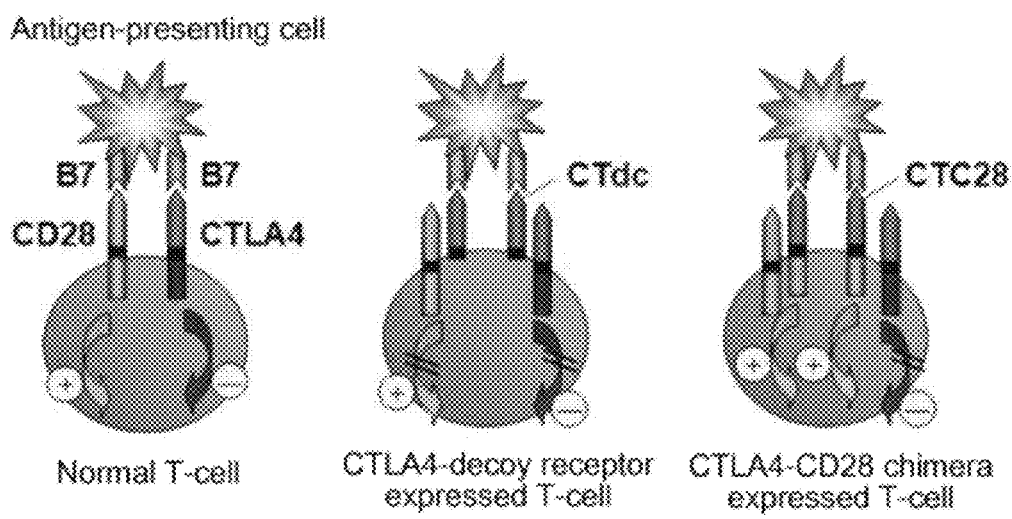
FIG. 1 shows the cancer treatment principle of a cancer antigen-specific T-cell expressing one embodiment of a CTLA4-CD28 chimera protein.

The present inventors have designed an anticancer T-cell genetically engineered so as to express a CTLA4-CD28 chimera protein, which includes CTLA4 lacking its intracellular inhibitory signaling domain and the intracellular stimulatory signaling domain of CD28 protein, fused to the receptor (see FIG. 1). When a ligand binds to CTLA4, a T-cell inhibitory signal caused by the binding between CTLA4 and the ligand is converted to a stimulatory signal by the action of the intracellular stimulatory signaling domain of CD28 in the CTLA4-CD28 chimera protein, and T-cell tolerance to cancer cells can be overcome and anticancer effects of the T-cell can be greatly enhanced by the activation thereof, and side effects such as the development of autoimmune disease caused by the systemic inhibition of CTLA4 activity can be minimized. In addition, according to the present invention, the activity of CTLA4 or PD1 that is expressed specifically in cancer cells can be inhibited, thus minimizing side effects such as autoimmune diseases which occur when a non-specific CTLA4 or PD1 antagonist such as existing anti-CTLA4 antibody is used.

Accordingly, a pharmaceutical composition for treating cancer, which includes a T-cell transduced with the CTLA4-CD28 chimera gene or PD1-CD28 chimera gene of the present invention, is useful for T-cell immunotherapy having significantly excellent effects on cancer treatment compared to existing methods.

The present invention also provides a pharmaceutical composition for treating cancer, which includes the transduced T-cell of the present invention.

The pharmaceutical composition for treating cancer according to the present invention includes a cancer antigen-specific CD4 T-cell or CD8 T-cell transduced with the CTLA4-CD28 chimera gene or the PD1-CD28 chimera gene. The composition of the present invention may include both a cancer antigen-specific CD4 T-cell and CD8 T-cell transduced with the CTLA4-CD28 chimera gene or the PD1-CD28 chimera gene.

Examples of the cancer or carcinoma that is treated according to the present invention include, but are not limited to, solid cancers and blood cancers. Examples thereof include, but are not limited to, stomach cancer, lung cancer, breast cancer, ovarian cancer, liver cancer, bronchial cancer, nasopharyngeal cancer, laryngeal cancer, pancreatic cancer, bladder cancer, colorectal cancer, colon cancer, cervical cancer, brain cancer, prostate cancer, bone cancer, skin cancer, thyroid cancer, parathyroid cancer, renal cancer, esophageal cancer, bile duct cancer, testicular cancer, rectal cancer, head and neck cancer, cervical cancer, ureter cancer, osteosarcoma, neuroblastoma, melanoma, fibrosarcoma, rhabdomyosarcoma, astrocytoma, neuroblastoma, and glioma. Other examples include colorectal cancer, ovarian cancer, stomach cancer, pancreatic cancer, and breast cancer.

The composition according to the present invention may further include pharmaceutically acceptable carriers. For oral administration, the composition may comprise a binder, a lubricant, a disintegrant, an excipient, a solubilizing agent, a dispersing agent, a stabilizer, a suspending agent, a pigment, fragrance, etc. For injection, the composition may include a buffer, a preservative, a pain-alleviating agent, a solubilizing agent, an isotonic agent, a stabilizer, etc. For topical application, the composition may include a base, an excipient, a lubricant, a preservative, etc. The pharmaceutical composition of the present invention may be formulated in various forms with the pharmaceutically acceptable carriers as described above. For example, for oral administration, the composition may be formulated in the form of tablets, troches, capsules, elixirs, suspensions, syrups, wafers, etc. For injection, the composition may be formulated in the form of unit dosage ampoules or multiple dosage containers. The anticancer composition may typically include a surfactant that facilitates delivery through the membrane. Examples of this surfactant include surfactants derived from steroids, cationic lipids such as N-[1-(2,3-dioleoyl)propyl-N,N,N-trimethylammonium chloride (DOTMA), and various compounds such as cholesterol hemisuccinate or phosphatidyl glycerol.

The present invention also provides a method for treating cancer and inhibiting cancer growth, which includes administering to a subject a composition having a cancer antigen-specific T-cell transduced with the CTLA4-CD28 chimera gene or PD1-CD28 chimera gene of the present invention.

The composition of the present invention can be administered in a pharmaceutically acceptable amount to treat cancer cells or their metastases or inhibit cancer growth. The dose of the composition can vary depending on various factors, including the kind of cancer, the patient's age and body weight, the severity of the disease, the kind of current therapy, the number of treatments, the mode and route of administration, etc., and can be easily determined by those skilled in the art. The composition of the present invention may be administered simultaneously or sequentially with the pharmacologically or physiologically active ingredient. In addition, the composition of the present invention may be administered in combination with conventional therapeutic agents and may be administered sequentially or simultaneously with conventional therapeutic agents. This dosage may be single or multiple doses. It is important to administer the minimum amount that can provide maximum effects without side effects, in view of all the above-described factors, and this amount can be readily determined by those skilled in the art.

Hereinafter, the present invention will be described in detail with reference to examples and experimental examples. It is to be understood, however, that these examples are for illustrative purposes only and are not intended to limit the scope of the present invention.

EXAMPLE 1

Preparation of Mice and Cells

Pmel-1, OT-I, B6, and Thy1.1+congenic B6 mice were obtained from the Jackson laboratory. OT-II mice on a Rag1−/− background were from the Taconic. All of the transgenic mice were on a B6 background. The mice were bred in a specific pathogen-free animal facility at the Research Institute National Cancer Center, Korea and maintained in accordance with the guidelines of the Institutional Animal Care and Use Committee.

E.G7 lymphoma cells and B16-F10 (B16) melanoma cells (ATCC Nos. CRL-2113 and CRL-6475) were derived from B6 mice. Phoenix Eco and Phoenix GP cell lines were obtained from ATCC under the approval of Garry Nolan (Stanford University) (ATCC Nos. SD3444 and SD3514).

CD8 T-cells or CD4$^+$CD25$^-$ T-cells were purified by positive selection using anti-CD8 microbeads or by negative selection using CD4+CD25-regulatory T cell isolation kit.

EXAMPLE 2

Plasmid Construction

To generate CTLA4-CD28 chimera, a nucleotide sequence (SEQ ID NO: 9) encoding the extracellular and transmembrane domain of mouse CTLA4 and a nucleotide sequence (SEQ ID NO: 10) encoding the intracellular domain of mouse CD28 were amplified by polymerase chain reaction (PCR) from the plasmids containing mouse CTLA4 and CD28 cDNA. The two amplified fragments were joined by blunt end ligation and were cloned into a cloning vector.

Subsequently, CTLA4-CD28 chimera cDNA was cloned into pMIG-w retroviral expression vector (FIG. 2(a)) (a gift from Yosef Refaeli, National Jewish Medical and Research Center, USA).

For the CTLA4-decoy receptor, a nucleotide sequence encoding the extracellular and transmembrane portion of CTLA4 (SEQ ID NO: 9) was amplified by PCR and was cloned into the pMIG-w retrovirus vector (see FIG. 2(b)).

with normal hamster IgG or hamster anti-mouse CTLA4 (2 µg/ml) antibody for 10 minutes on ice, followed by cross-linking with goat anti-mouse IgG or anti-hamster IgG (5 µg/ml) for 10 minutes on ice. Then, cells were placed in a 37° C. water bath for 30 minutes and the reaction was stopped by adding ice-cold PBS. The cell lysates were subjected to SDS-PAGE, transferred to a nitrocellulose membrane (Millipore), and probed with anti-phospho-Akt or anti-Akt antibody (Cell Signaling). Horseradish peroxidase-conjugated (HRP-conjugated) secondary antibodies (Jackson Immunoresearch Laboratories) were used to detect primary antibodies. Blots were visualized by chemiluminescence reaction using SuperSignal West Pico (Pierce).

TABLE 2

Polynucleotide sequences used in the present invention

| No | Seq. Nature | Sequence |
|---|---|---|
| 9 | CTLA4 murine (extracellular and transmembrane domain | atggcttgtc ttggactccg gaggtacaaa gctcaactgc agctgccttc taggacttgg cctttgtag ccctgctcac tcttcttttc atcccagtct tctctgaagc catacaggtg acccaacctt cagtggtgtt ggctagcagc catggtgtcg ccagctttcc atgtgaatat tcaccatcac acaacactga tgaggtccgg gtgactgtgc tgcggcagac aaatgaccaa atgactgagg tctgtgccac gacattcaca gagaagaata cagtgggctt cctagattac cccttctgca gtggtacctt taatgaaagc agagtgaacc tcaccatcca aggactgaga gctgttgaca cgggactgta cctctgcaag gtggaactca tgtacccacc gccatacttt gtgggcatgg gcaacgggac gcagatttat gtcattgatc cagaaccatg cccgattct gacttcctcc tttggatcct tgtcgcagtt agcttggggt tgtttttta cagtttcctg gtcactgctg tttctttgag caagatg (SEQ IS NO: 9) |
| 10 | CD28 murine (intracellular domain | acaaatagta gaaggaacag actccttcaa agtgactaca tgaacatgac tccccggagg cctgggctca ctcgaaagcc ttaccagccc tacgcccctg ccagagactt tgcagcgtac cgcccctga (SEQ IS NO: 10) |

EXAMPLE 3

Luciferase Assay and Western Blot

Jurkat T cells (1×10⁷) were mixed with retroviral expression plasmid, RE/AP luciferase plasmid (a gift from Arthur Weiss, University of California), and pRL-TK Renilla luciferase control plasmid for normalization (Promega).

Then, the cells were transformed by electroporation at 250V and 950 µF in a 0.4-cm-gap cuvette using Gene Pulser (Bio-Rad Laboratories).

After transformation, the cells were allowed to stand for 24 hours before stimulation. For stimulation, a 96-well-plate was coated with goat anti-mouse IgG (5 µg/ml) plus anti-hamster IgG (5 µg/ml) overnight, then was washed and coated with anti-CD3 (1 µg/ml) along with normal hamster IgG or hamster anti-mouse CTLA4 (9H10, 2 µg/ml) for 2 hours at room temperature.

Then, 1×10⁵ cells were added to each well and incubated at 37° C. for 6 hours, followed by lysis. For some experiments, soluble anti-CD28 was added to the stimulation culture directly instead of plate-bound anti-CTLA4.

Luciferase activity was measured with a luminometer (Promega) using a Dual-luciferase reporter assay system. Firefly luciferase activity was normalized to Renilla luciferase activity.

For western blot analysis, the retroviral plasmids without luciferase plasmids were used in the above transfection protocol to transfect Jurkat T cells.

For stimulation of the transfected cells, the cells were treated either with mouse anti-human CD28 antibody or

EXAMPLE 4

Production and Transduction of Retrovirus

The retroviral plasmids and a plasmid encoding VSV-G cDNA (pMD.G) were transiently transfected into Phoenix GP cell line using Lipofectamine 2000 (Invitrogen). After 48 hours, Phoenix Eco cell line was transduced with the culture supernatant containing VSV-G pseudotyped retrovirus for overnight.

After 3-5 days, GFP-positive Phoenix Eco cells were purified via a cell sorter (FACS Aria, BD Biosciences) to generate stable cell lines for producing ecotropic retroviruses. The culture supernatant containing ecotropic retrovirus was harvested and then concentrated 10-fold using a centrifugal filter device (Amicon Ultra-15, 100 kDa cut-off, Millipore). For retroviral transduction of T cells, spleen cells from normal mice or the transgenic mice were stimulated by plate-bound anti-CD3 (5 µg/ml, 145-2C11) and anti-CD28 (2 µg/ml, 37.51) antibodies or antigenic peptides.

24 h after stimulation, T cells were transduced with the concentrated retroviruses by centrifuging the cells at 2500 rpm for 90 minutes (i.e., spin infection). This procedure was repeated once on the same day. During the spin infection, 6 µg/ml polybrene (Sigma) was added to the culture supernatant, or the cells were transduced in a Retronectin-coated plate (15 µg/ml, Takara) to enhance the transduction efficiency. 48 hours after stimulation, the transduced T cells were transferred to a fresh medium containing 30 unit/ml mouse IL-2 (Invitrogen) and were rested for 48-72 hours without further stimulation before analysis.

EXAMPLE 5

Cytokine ELISA, Cell Proliferation, and Cell Cytotoxicity Assay (P-JAM Test)

GFP-positive T-cells purified by cell-sorting ($2\times10^4$/well) were stimulated with various concentrations of anti-CD3 antibody or antigenic peptides in the presence of irradiated splenocytes ($2\times10^5$/well) for 48 hours.

The cytokines in the supernatant were measured using ELISA sets (BD Biosciences).

To measure cell proliferation, 48 hr-stimulated cells were pulsed with $^3$H-Thymidine for additional 24 hours. Cells were harvested using a cell harvester, and radioactivity was counted in a Wallac Trilux 1450 scintillation counter.

For cell cytotoxicity assay, the transduced Pmel-1 T cells were stimulated with 1 µM hgp100 peptide in the presence of irradiated splenocytes for 48 hours. The various numbers of activated T-cells were co-cultured with B16 cells ($1\times10^4$) for 20 hours and then washed off with PBS. The remaining B16 cells were pulsed with $^3$H-Thymidine for 6 hours, harvested and radioactivity was measured.

EXAMPLE 6

Adoptive T-Cell Transfer

B6 mice were injected subcutaneously with E.G7 cells ($1$-$2\times10^6$) or B16 cells ($1\times10^5$) on day 0. The retrovirus-transduced T-cells were adoptively transferred into the mice on day 7. For the B16 melanoma models, the mice were lymphodepleted by nonmyeloablative (4 Gy) total body irradiation (TBI) on the day of cell transfer.

Tumor growth was measured using a caliper every 3 to 4 days and their approximate sizes (mm$^2$) were calculated using the following formula: length (mm)×width (mm)×π. The mice were euthanized when the tumor size exceeded 500 mm$^2$. For intracellular cytokine staining for the transduced T-cells, the ex vivo activated T-cells were fixed and permeabilized (BD cytofix/cytoperm kit), and stained with PE-labeled anti-mouse IL-2 or IFN-γ.

EXPERIMENTAL EXAMPLE 1

T-Cell Activating Effect of CTLA4-CD28 Chimera Protein

As shown in FIG. 2(*b*), a retroviral construct was assembled, which expresses a CTLA decoy receptor that is a CTLA4 mutant lacking the intracellular inhibitory signaling domain of mouse CTLA4 (see SEQ ID NO: 2), and a CTLA4-CD28 chimera protein (see SEQ ID NO: 6).

In FIGS. 2(*a*) and 2(*b*), EV is the empty retroviral vector (pMIG-w), and the CTLA4-CD28 chimera (CTC28) gene or CTLA4 decoy receptor (CTdc) cDNA was inserted in front of IRES-GFP (green fluorescence protein) cassette of pMIG-w.

When Jurkat T-cells transduced with an empty plasmid containing no CLTA4 decoy receptor or CTLA4-CD28 chimera receptor or an RE/AP luciferase plasmid containing a CD28 response element were stimulated with anti-CD3 and anti-CD28 antibodies, luciferase activity greatly increased compared to that with anti-CD3 alone as previously reported (see FIG. 3(*a*)), indicating that signals from endogenous CD28 were successfully delivered).

Likewise, when Jurkat cells were transfected with a CTLA4-CD28 chimera gene plasmid and the RE/AP luciferase plasmid and stimulated with anti-CD3 and anti-CTLA4 antibody, a remarkable increase in luciferase activity was observed compared with anti-CD3 stimulation alone. In contrast, transfection of the cells with CTLA4 decoy plasmid failed to enhance luciferase activity (see FIG. 3(*b*)).

When Jurkat cells transfected with CTLA4-CD28 chimera were stimulated with anti-CTLA4, Akt phosphorylation increased, whereas CTLA4 decoy-transfected Jurkat cells did not show any increase in Akt phosphorylation (see FIG. 11).

This demonstrates that, when the CTLA4-CD28 chimera protein is used, a stimulatory signal by CD28 is transduced into cells even when a ligand binds to the extracellular domain of CTLA4.

This is demonstrated by the result of T-cell activation. As shown in FIG. 2(*b*), when activation of T-cells was measured using GFP as a reporter, T-cells transduced with CTLA4 decoy gene showed reduced cell division and IFN-γ secretion, whereas T-cells transduced with CTLA4-CD28 chimera gene showed significantly increased IFN-γ secretion together with normal division (see FIGS. 3(*c*) and 3(*d*)).

Also, spleen cells were transduced with an empty plasmid containing no CTLA4-CD28 chimera gene and a plasmid containing a CD28 response element and having a GFP reporter gene, and were stained with anti-CD28 and anti-CTLA4 antibody, and GFP positive cells were analyzed using a flow cytometer. As a result, it was shown that the expression level of CTLA4-CD28 chimera was higher than the expression level of endogenous CTLA4 (see FIG. 12).

In addition, it was shown that, when the spleen T-cells transduced as described above were stimulated with anti-CD3, anti-CD28, and anti-CTLA4 antibody, overexpression of CTLA4-CD28 reduced the IFN-γ inhibitory ability of anti-CTLA4 antibody (see FIG. 13).

From the above-described results, it can be seen that the CTLA4-CD28 chimera protein does not deliver an inhibitory signal when a ligand binds to the extracellular domain of CTLA4, and that a stimulatory signal by the intracellular domain of CD28 of the CTLA4-CD28 chimera protein is delivered into cells, thereby significantly increasing the activation of T-cells.

EXPERIMENTAL EXAMPLE 2

Anticancer Ability of CD8 T-Cells Transduced with CTLA4-CD28 Chimera Gene

In order to test if the expression of CTLA4-CD28 chimera gene in tumor antigen-specific T-cells can enhance the anti-tumor activity of the T-cells, the CTLA4-CD28 chimera-encoding retrovirus was transduced into CD8 T cells from the melanoma antigen-specific TCR transgenic mice called Pmel-1. Pmel-1 T-cells recognize a tumor antigen, gp100, which expresses in syngenic B16 melanoma cells.

As a result, although the transduced Pmel-1 T-cells showed high IFN-γ secretion compared to Pmel-1 T cells (see FIG. 4(*a*)), they did not show any enhancement of cytolytic activity on B16 cells in vitro (see FIG. 4(*b*)). Also, when CTLA4-CD28 chimera-transduced Pmel-1 T-cells were adoptively transferred to lymphodepleted B16 tumor-bearing mice in combination with high doses of IL-2, they did not enhance an anti-tumor effect of the T-cells (see FIG. 4(*c*)). Thus, unlike the results of Experimental Example 1, CTLA4-CD28 chimera gene modification of Pmel-1 T cells did not show a huge enhancement of T-cell function.

EXPERIMENTAL EXAMPLE 3

Change in Response-to-Antigen of Antigen-Specific T-Cells by Transduction with CTLA4-CD28 Chimera Gene The difference between Experimental Examples 1 and 2 is that the T-cells from normal mice are a mixture of CD4 and CD8 T-cells, whereas Pmel-1 T-cells are pure CD8 T-cells alone. Thus, there is a need to examine whether the tumor antigen-specific response of CD4 and CD8 T cells would be differentially regulated by CTLA4-CD28 chimera gene modification. In order to examine CD4 and CD8 T cell responses to the same antigen, the present inventors adopted anti-OVA TCR transgenic mice constructed to express TCR, which specifically recognizes ovalbumin (OVA), only in T-cells. Particularly, to examine the responses of CD4 and CD8 T-cells, OVA-specific CD4 and CD8 cells were isolated from CD4 anti-OVA TCR transgenic mice (OT-II) and CD8 anti-OVA TCR transgenic mice (OT-I), respectively, and transduced with CTLA4-CD28 chimera gene, and then the activation of T-cells by OVA antigen was analyzed based on the production of IL2 and IFN-γ.

OT-I and OT-II T-cells transduced with CTLA4-CD28 chimera encoding retrovirus were stimulated with ovalbumin peptides in the presence of antigen presenting cell (APCs) in order to produce the production of cytokines. In the present invention, the term "OT-I CTC28" or "OT-II CTC28" means the OT-I T-cells or OT-II T-cells transformed with CTLA4-CD28 chimera gene.

As a result, it could be seen that CTLA4-CD28 chimera gene-modification enhanced IFN-γ production in both OT-I (see FIG. 5(d)) and OT-II T cells (see FIG. 5(b)).

Also, IL-2 production of OT-II T-cells 10- to 20-fold increased compared to control cells (FIG. 5(a)), although the amount of the cytokine produced was very small (FIG. 5(c)). In other words, CD4 T-cell response was more affected by the gene-modification than CD8 T cell response, especially in terms of IL-2 production.

EXPERIMENTAL EXAMPLE 4

Anti-Tumor Effect of T-Cells by Transduction of CTLA4-CD28 Chimera Gene into Both CD4 and CD8 T-Cells It is well-known that CD4 T-cells are necessary for anti-tumor effects of CD8 T cells. Therefore, enhanced CD4 response to a tumor antigen can facilitate anti-tumor effects of tumor antigen-specific CD8 T-cells.

The present inventors examined whether CTLA4-CD28 gene-modification of CD4 T-cells enhances anti-tumor effects of CD8 T-cells, using the OT-I and OT-II T cells in Experimental Example 3. In order to use ovalbumin as a model tumor antigen, a syngenic EL4 lymphoma cell line transfected with ovalbumin cDNA (E.G7) was selected as a tumor model (see FIG. 6).

When OT-II T-cells transduced with CTLA4-CD28 chimera gene were adoptively transferred to E.G7-bearing mice, no anti-tumor effect was (see FIG. 7).

However, when the OT-II T-cells were combined with OT-I T-cells, the effect thereof changed. The use of OT-I T-cells alone showed a slight effect, but the use of OT-I T-cells in combination with the OT-II T-cells transduced with CTLA4-CD28 chimera gene showed significantly increased anti-tumor effects, and this increase was proportional to the level of the OT-II T-cells transduced with CTLA4-CD28 chimera gene (see FIGS. 8(a) to 8(c), and FIG. 14).

Particularly, when OT-I T-cells and the transduced OT-II T-cells were used at a ratio of 2:2, the tumor completely disappeared after 15 days. When they were used at a ratio of 2:1, the tumor almost disappeared after 15 days, wherein the tumor volume slightly increased again.

In the above experiment, the mean tumor size of at least five mice per group was recorded. (*, p=0.0391; , p=0.0078; *, p=0.0078, Wilcoxon matched-pairs test). The results in FIGS. 7 and 8 are representative of at least two independent experiments.

It could be seen through the above Experimental Example that transduction with CTLA4-CD28 chimera gene increases the response of CD8 T-cells to antigen, although the CD8 T-cells are less effective than CD4 T-cells. Thus, in order to examine whether the transduction of both CD4 and CD8 T-cells with CTLA4-CD28 chimera gene can maximize their anti-tumor effects, both OT-II T-cells and OT-I T-cells were transduced with CTLA4-CD28 chimera gene and then injected into mice having E.G7 tumor (FIG. 6). As a result, it could be seen that these cells showed more potent anti-tumor effects than the transduced OT-II T-cells alone (FIG. 9).

In the above experiment, the mean tumor size of at least five mice per group was recorded. (*: p=0.0029, Wilcoxon matched-pairs test). The results in FIG. 9 are representative of at least three independent experiments.

To examine the reactivity of the gene-transduced T-cells in E.G7 tumor-bearing mice, splenocytes were isolated from the mice injected with the gene-modified OT-I and OT-II T-cells, and were stimulated ex vivo with ovalumin (OVA) peptides. The gene-transduced OT-II T-cells showed much higher percentages of both IL-2 and IFN-γ producing cells than control OT-II T-cells when analyzed by intracellular cytokine staining (see FIGS. 15(a) and 15(b)). Also, the total number of the gene-transformed OT-II T-cells increased compared to control OT-II T-cells (see FIG. 15(c)). With the OT-I T-cells, the percentage of the gene-transduced OT-I T-cells in the spleen was too low to allow analysis by intracellular cytokine staining (i.e., approximately 0.1%). Therefore, the present inventors purified total CD8 T-cells and stimulated the equal numbers of the gene-transduced and empty vector-transduced OT-I T-cells with ovalbumin peptide plus APCs in vitro. Also, IFN-γ production was measured by ELISA. Again, the gene-transduced OT-I T-cells produced larger amounts of IFN-γ than empty vector-transformed OT-I T-cells (see FIG. 15(d)). Thus, it could be seen that the gene-transduced OT-I and OT-II T-cells retained their enhanced reactivity in tumor-bearing mice.

EXPERIMENTAL EXAMPLE 5

Anti-Tumor Effects of Tumor Antigen-Specific T-Cells Transduced with CTLA4-CD28 Chimera Gene in Melanoma Model Because the model in Experimental Example 4 was used to test antitumor effects against the artificial tumor antigen OVA, it is required to test antitumor effects in a model bearing an actual tumor antigen using the CD4 and CD8 T-cells transduced with the CTLA4-CD28 chimera gene.

B16 melanoma is one of suitable tumor models because it has endogenous gp100 antigen that could be recognized specifically by Pmel-1 CD8 T-cells. However, B16 tumor has been reported to have poor immunogenicity and resistance to T-cells immunotherapy. Consistently, when Pmel-1 T-cells transduced with CTLA4-CD28 chimera according to the present invention were used, improvement in antitumor effects was not insignificant (see Experimental Example 2). Nonetheless, T-cell immunotherapy using Pmel-1 T-cells in combination with polyclonal CD4 T-cells has been shown to be effective.

In this experiment, the present inventors examined whether the use of CTLA4-CD28 chimera gene-transduced Pmel-1 T-cells in combination with CTLA4-CD28 chimera gene-transduced polyclonal CD4 T-cells shows enhanced antitumor effects.

B16 melanoma cells were injected subcutaneously into B6 mice, and 7 days thereafter, the mice were subjected to lymphocyte depletion by systemic irradiation of 5 Gy. Then, Pmel-1 T-cells (melanoma-specific CD8 T-cells) isolated from transgenic mice were injected intravenously into the B6 mice, and a reduction in the volume of the tumor in the mice was observed.

Also, polyclonal CD4 T-cells (regulatory T cell-depleted $CD4^+CD25^-$) isolated from B6 mice were transduced with CTLA4-CD28 chimera gene and used in combination with Pmel-1 T-cells.

As a result, it was shown that, when both CD4 T-cells and Pmel-1 T-cells were transduced with the CTLA4-CD28 chimera gene and injected intravenously into B16 tumor-bearing B6 mice, they showed significantly more potent antitumor effects than untransduced CD4 T-cells and Pmel-1 T-cells on the basis of tumor size and survivability (see FIGS. 10(a) and 10(b)). Also, such antitumor effects were closely associated with increases in the percentages and absolute numbers of the transduced CD4 T-cells and Pmel-1 T-cells in the peripheral blood (see FIGS. 16(a) to 16(d)).

The T-cell proliferation effect of the CTLA4-CD28 chimera gene was higher in CD4 T-cells than in CD8 T-cells (viz., 8.6 fold versus 3.7 fold; see FIGS. 16(c) to 16(d)). The present inventors checked whether gene-modification of CD4 T-cells alone can increase the anti-tumor effect of Pmel-1 T-cells. As expected, the modified CD4 T-cells substantially enhanced tumor regression. Additional gene-modification of Pmel-1 T-cells further enhanced tumor regression (see FIG. 17). Thus, it could be seen that gene-modification of both CD4 and CD8 T-cells can maximize their antitumor effects. Finally, since CTLA4-CD28 modification significantly increased IL-2 secretion in CD4 T-cells (FIG. 5(a)), the present inventors wondered if IL-2 is essential for therapeutic effect of the gene-modified T-cells in vivo. As expected, upon anti-IL-2 neutralizing antibody treatment in vivo, the therapeutic effect of gene-modification was nearly abrogated (see FIG. 18). Collectively, these results show that poorly immunogenic, pre-established syngenic tumors can be efficiently regressed by adoptive transfer therapy with CTLA4-CD28 gene-modified CD4 and CD8 T-cells through an IL-2-dependent mechanism, and IL-2 plays an important role in this therapeutic effect. As used herein, the term "Pmel-1 EV" means untransduced Pmel-1 T-cells; "CD4 EV" means untransduced CD4; "Pmel-1 CTC28" means Pmel-1 T-cells transduced with CTLA4-CD28 chimera gene; and "CD4 CTC28" means CD4 T-cells transduced with CTLA4-CD28 chimera gene.

In conclusion, T-cell immune therapy using T-cells transduced with CTLA4-CD28 chimera gene shows significantly enhanced antitumor effects in anticancer therapy using a combination of CD4 and CD8 T-cells, suggesting that the efficacy of anticancer T-cell immunotherapy can be significantly increased by preventing T-cell tolerance from being caused by the CTLA4 receptor.

The invention claimed is:

1. An isolated nucleic acid encoding a fusion protein, said fusion protein comprising:
   (i) a T-cell surface tolerance-inducing receptor lacking its intracellular signaling domain; and
   (ii) an intracellular signaling domain of the CD28 protein, wherein the fusion protein had the amino acid sequence set fourth in SEQ ID NO: 5 or 7.

2. The isolated nucleic acid of claim 1, further comprising an extracellular domain and transmembrane domain, wherein both domains are from the CTLA4 protein and are encoded by the nucleic acid set forth in SEQ ID NO: 9.

3. The isolated nucleic acid of claim 1, wherein the intracellular domain of the CD28 protein is encoded by the nucleic acid sequence set forth by SEQ ID NO: 10.

4. A viral vector comprising the nucleic acid of claim 1.

5. The viral or carrier of claim 4, wherein the viral carrier is any one selected from the group consisting of retrovirus, lentivirus, adenovirus, and adeno-associated virus.

6. An isolated T-cell transduced with the viral vector of claim 4.

7. The isolated T-cell of claim 6, wherein the T-cell is a cancer antigen-specific CD4 T-cell, a cancer antigen-specific CD8 T-cell, or a combination of a cancer antigen-specific CD4 T-cell and a cancer antigen-specific CD8 T-cell.

8. The isolated T-cell of claim 6, wherein the T-cell is a cancer antigen-specific T-cell.

9. The isolated T-cell of claim 8, wherein the cancer antigen-specific T-cell is any one selected from the group consisting of a T-cell isolated from the cancer tissue of a patient, a T-cell transduced with a receptor gene that recognizes cancer antigen, and a T-cell transduced with chimeric antigen receptor (CAR) gene.

10. The isolated T-cell of claim 8, wherein the cancer antigen is any one selected from the group consisting of MUC1, CD19, HER2, EGFR, CD20, CEA, PSMA, GD2, folate receptor, IL-13Ra2, Lewis-Y antigen, NY-ESO-1, MART-1, gp100, tyrosinase, tyrosinase-related proteins, MAGE, and WT-1.

11. A pharmaceutical composition for treating cancer, comprising the transduced T-cell of claim 6.

12. The pharmaceutical composition of claim 11, wherein the transduced T-cell comprises a cancer antigen-specific CD4 T-cell, a cancer antigen-specific CD8 T-cell, or a combination of a cancer antigen-specific CD4 T-cell and a cancer antigen-specific CD8 T-cell.

13. An in vitro method for producing the transduced T-cell of claim 6, the method comprising transducing an isolated T-cell with the viral carrier of claim 4.

* * * * *